US009012198B2

(12) United States Patent
Sene et al.

(10) Patent No.: US 9,012,198 B2
(45) **Date of Patent: *Apr. 21, 2015**

(54) METHOD FOR ORTHOPOXVIRUS PRODUCTION AND PURIFICATION

(71) Applicant: Transgene S.A., Illkirch Graffenstaden (FR)

(72) Inventors: Claude Sene, Strasbourg (FR); Sylvie Campourcy, Strasbourg (FR); Yves Cordier, Strasbourg (FR)

(73) Assignee: Transgene S.A., Illkirch (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/077,621

(22) Filed: Nov. 12, 2013

(65) Prior Publication Data

US 2014/0073033 A1 Mar. 13, 2014

Related U.S. Application Data

(63) Continuation of application No. 13/319,874, filed as application No. PCT/EP2010/056491 on May 11, 2010, now Pat. No. 8,609,392.

(60) Provisional application No. 61/213,484, filed on Jun. 12, 2009.

(30) Foreign Application Priority Data

May 12, 2009 (EP) .................................... 09305422

(51) Int. Cl.

| | |
|---|---|
| ***C12N 7/02*** | (2006.01) |
| ***C12N 7/00*** | (2006.01) |
| ***C12N 15/86*** | (2006.01) |
| ***C12P 21/00*** | (2006.01) |

(52) U.S. Cl.

CPC *C12N 7/025* (2013.01); *C12N 7/02* (2013.01); *C12N 7/00* (2013.01); *C12N 2710/24152* (2013.01); *A61K 35/768* (2013.01); *C12N 15/86* (2013.01); *C12N 2710/24251* (2013.01); *C12P 21/00* (2013.01)

(58) Field of Classification Search

CPC ............ C12N 2710/24151; C12N 2710/24152
See application file for complete search history.

(56) References Cited

U.S. PATENT DOCUMENTS

| | | | | |
|---|---|---|---|---|
| 4,675,187 | A | 6/1987 | Konishi et al. | |
| 5,861,381 | A | 1/1999 | Chambon et al. | |
| 5,879,924 | A | 3/1999 | Foster et al. | |
| 6,007,806 | A | 12/1999 | Lathe et al. | |
| 6,596,533 | B1 | 7/2003 | Erbs et al. | |
| 6,884,786 | B1 | 4/2005 | Kieny et al. | |
| 7,049,117 | B2 | 5/2006 | Erbs et al. | |
| 7,118,754 | B1 | 10/2006 | Balloul et al. | |
| 7,332,478 | B2 | 2/2008 | Kieny et al. | |
| 7,488,482 | B2 | 2/2009 | Balloul et al. | |
| 7,572,438 | B2 | 8/2009 | Erbs et al. | |
| 7,670,607 | B2 | 3/2010 | Balloul et al. | |
| 7,695,960 | B2 | 4/2010 | Inchauspe et al. | |
| 8,003,363 | B2 * | 8/2011 | Djurup et al. | 435/239 |
| 8,057,162 | B2 | 11/2011 | Fournillier et al. | |
| 8,173,021 | B2 * | 5/2012 | Wolff et al. | 210/651 |
| 2006/0134065 | A1 | 6/2006 | Fournillier | |
| 2010/0008941 | A1 | 1/2010 | Fournillier et al. | |
| 2010/0316610 | A1 | 12/2010 | Erbs et al. | |
| 2011/0165645 | A1 * | 7/2011 | Xiong | 435/173.9 |

FOREIGN PATENT DOCUMENTS

| | | |
|---|---|---|
| WO | WO 88/07378 | 10/1988 |
| WO | WO 90/10459 | 9/1990 |
| WO | WO 91/11201 | 8/1991 |
| WO | WO 92/07000 | 4/1992 |
| WO | WO 94/29471 | 12/1994 |
| WO | WO 95/09241 | 4/1995 |
| WO | WO 98/04705 | 2/1998 |
| WO | WO 99/03855 | 1/1999 |
| WO | WO 99/54481 | 10/1999 |
| WO | WO 2004/020971 | 3/2004 |
| WO | WO 2004/111082 | 12/2004 |

(Continued)

OTHER PUBLICATIONS

Wolff et al (Biotechnology and Bioengineering 105:761-769, 2010, published online Nov. 4, 2009).*
International Search Report mailed on Aug. 2, 2010, issued in corresponding PCT Application PCT/EP2010/056491.
G. Antoine et al., *The Complete Genomic Sequence of the Modified Vaccinia Ankara Strain: Comparison with Other Orthopoxviruses*, 244 Virology 365-396 (1998).
Z.D. Ezzeddine et al., *Selective Killing of Glioma Cells in Culture and in Vivo by Retrovirus Transfer of the Herpes Simplex Virus Thymidine Kinase Gene*, 3(6) The New Biologist 608-614 (1991).
S. Goebel et al., *The Complete DNA Sequence of Vaccinia Virus*, 179 Virology 247-266 (1990).
S. Goebel et al., *Appendix to "The Complete DNA Sequence of Vaccinia Virus,"* 179 Virology 517-563 (1990).
I. Ivanov et al., *Establishment and characterization of a permanent duck embryo cell line*, Experimental Pathology and Parasitology 41-44 (Apr. 2000).

(Continued)

*Primary Examiner* — Mary E Mosher
(74) *Attorney, Agent, or Firm* — Buchanan Ingersoll & Rooney PC

(57) ABSTRACT

The present invention relates to a method for producing and purifying a wild type, an attenuated and/or a recombinant Orthopoxvirus. The present invention relates to a purified wild type, attenuated and/or recombinant Orthopoxvirus obtained by the method of the invention and to a pharmaceutical composition, preferably a vaccine, comprising said purified Orthopoxvirus for the treatment and/or the prevention a cancer, an infectious disease and/or an autoimmune disorder, and uses thereof. The present invention also relates to the use of an immortalized avian cell line obtained from an avian cell belonging to the Anatidae family, in particular *Cairina moschata* immortalized avian cell lines comprising a nucleic acid sequence coding a telomerase reverse transcriptase (TERT) and optionally an E1A nucleic acid sequence, for the production of a wild type, attenuated and/or recombinant Orthopoxvirus according to the process of the invention.

71 Claims, 7 Drawing Sheets

(56) References Cited

FOREIGN PATENT DOCUMENTS

| | | |
|---|---|---|
| WO | WO 2005/007840 | 1/2005 |
| WO | WO 2005/007857 | 1/2005 |
| WO | WO 2005/080556 | 9/2005 |
| WO | WO 2006/042414 | 4/2006 |
| WO | WO 2007/077256 | 7/2007 |
| WO | WO 2007/121894 | 11/2007 |
| WO | WO 2007/147528 | 12/2007 |
| WO | WO 2008/138533 | 11/2008 |
| WO | WO 2009/004016 | 1/2009 |
| WO | WO 2009/065546 | 5/2009 |
| WO | WO 2009/065547 | 5/2009 |
| WO | WO 2009/100521 | 8/2009 |

OTHER PUBLICATIONS

G. Johnson et at, *An Update on the Vaccinia Virus Genome*, 196 Virology 381-401 (1993).

I. Knezevic et al, *WHO Study Group on cell substrates for production of biological, Geneva Switzerland*, Jun. 11-12, 2007, 36 Biologicals 203-211 (2008).

G. Kotwal et al., *Growing Poxviruses and Determining Virus Titer—Poxvirus Growth, Purification, and Titering*, 269 Methods in Molecular Biology 101-112 (2004).

A. Kumar et al., *Purification, potency and immunogenicity analysis of Vero cell culture-derived rabies vaccine: a comparative study of single-step column chromatography and zonal centrifuge purification*, 7 Microbes and Infection 1110-1116 (2005).

F. Lamb et al., *Nucleotide sequence of cloned cDNA coding for preproricin*, 148 Eur. J. Biochem. 265-270 (1985).

M. Liu et al., *Gene-based vaccines and immunotherapeutics*, 101(2) PNAS 14567-14571 (Oct. 5, 2004).

R.J. Massey, *Catalytic antibodies catching on*, 328 Nature 457-458 (Jul. 30, 1987).

A. Mayr et al., Passage history, properties and applications of the attenuated vaccinia virus strain MVA, 3(1) Infection 6-14 (1975).

F. Moolten, *Tumor Chemosensitivity Conferred by Inserted Herpes Thymidine Kinase Genes: Paradigm for a Prospective Cancer Control Strategy*, 46 Cancer Research 5276-5281 (Oct. 1986).

C. Mullen et al., *Transfer of the bacterial gene for cytosine deaminase to mammalian cells confers lethal sensitivity to 5-fluorocytosine: A negative selection system*, 89 Proc. Natl. Acad. Sci. USA 33-37 (Jan. 1992).

G. Richards et al., *Evaluation of a Cross-Flow Filtration Technique for Extraction of Polioviruses from Inoculated Oyster Tissue Homogenates*, 4 Journal of Virological Methods 147-153 (1982).

C. Rochlitz et al., *Phase I immunotherapy with a modified vaccinia virus (MVA) expressing human $MUC_1$ as antigen-specific immunotherapy in patients with $MUC_1$-positive advanced cancer*, 5 The Journal of Gene Medicine 690-699 (2003).

G. Smith et al., *The formation and function of extracellular enveloped vaccinia virus*, 83 Journal of General Virology 2915-2931 (2002).

Wolff et al., *Capturing of Cell Culture-Derived Modified Vaccinia Ankara virus by Ion Exchange and Pseudo-Affinity Membrane Adsorbers*, 105(4) Biotechnology and Bioengineering 761-769 (2010).

* cited by examiner

X4

X10

X20

X4

X10

X20

METHOD FOR ORTHOPOXVIRUS PRODUCTION AND PURIFICATION

TECHNICAL FIELD

The present invention pertains to the field of virus production and purification. In particular, the invention relates to a method for producing and purifying a wild type, an attenuated and/or a recombinant Orthopoxvirus.

BACKGROUND OF THE INVENTION

Orthopoxviruses are complex enveloped viruses having a diameter comprised between 200 and 300 nm that distinguish them principally by their unusual morphology, their large DNA genome and their cytoplasmic site of replication. The genome of several members of Orthopoxviruses, including the Copenhagen Vaccinia Virus (VV) strain (GOEBEL et al., 1990, Virol. 179, 247-266 and 517-563; JOHNSON et al., 1993, Virol. 196, 381-401) and the modified Vaccinia Virus Ankara (MVA) strain (ANTOINE et al., 1998, Virol. 244, 365-396), have been mapped and sequenced. VV has a double-stranded DNA genome of about 192 kb coding for about 200 proteins of which approximately 100 are involved in virus assembly. MVA is a highly attenuated Vaccinia Virus strain generated by more than 500 serial passages of the Ankara strain of Vaccinia Virus on chicken embryo fibroblasts (MAYR et al., 1975, Infection 3, 6-16). The MVA virus was deposited before Collection Nationale de Cultures de Microorganismes (CNCM) under depositary $N^{602}$ I-721. Determination of the complete sequence of the MVA genome and comparison with the Copenhagen VV genome allows the precise identification of the alterations which occurred in the viral genome and the definition of seven deletions (I to VII) and numerous mutations leading to fragmented ORFs (Open Reading Frame) (ANTOINE et al., 1998, Virology 244, 365-396).

The use of Orthopoxviruses as vectors for the development of recombinant live vaccines has been affected by safety concerns and regulations. Before using Orthopoxviruses for vaccination it is necessary to purify the viruses. Available Orthopoxviruses production methods comprise the replication of the virus in a cell line (e.g. HelaS3), in embryonated eggs or in Chicken Embryo Fibroblasts (CEFs). After the replication of the virus, the culture media is discard, the cells are lysed and the Orthopoxviruses released from the cells are purified by sucrose cushion centrifugation (KOTWAL and ABRAHAM; poxvirus growth, Purification and tittering in Vaccinia Virus and Poxvirology, 2004, 101-108, Humana Press Inc., Totowa; N.J.; USA). International patent application WO 07/147528 describes a method for producing a wild type, an attenuated and/or a recombinant MVA with no targeted infection specificity, comprising preparing a culture of packaging cells (e.g. CEFs; cell lines), infecting said cell culture, culturing said infected cells, recovering the MVAs produced from the culture supernatant and/or the packaging cells, and further purifying the viruses by depth filtration, microfiltration and diafiltration. WO 07/147528 specifies that when depth filtration, microfiltration and diafiltration are performed, the use of nucleases and more particularly, the use of Benzonase® as nuclease is not necessary.

International patent application WO 08/138533 describes a method for the purification of biologically active vaccinia virus, comprising loading a solid-phase matrix to which a ligand is attached with a vaccinia virus contained in a liquid-phase culture, washing the matrix, and eluting the virus.

Despite the description of several methods for Orthopoxvirus production and purification, a need remains for alternative. The present invention provides such methods.

DISCLOSURE OF THE INVENTION

As used throughout in the entire application, an "Orthopoxvirus" refers to a variola virus; a Vaccinia Virus (VV) such as for instance the Vaccinia virus strains: Elstree, Western Reserve, Wyeth, NYVAC, NYCBOH, Paris, Copenhagen; and their derivatives such as for instance a modified Vaccinia Virus Ankara (MVA) in particular MVA 575 (ECACC V00120707) and MVA-BN (ECACC V00083008). According to the invention the Orthopoxvirus can be indifferently an immature virus (IV), an intracellular mature virus (IMV), an intracellular enveloped virus (IEV), a cell-associated enveloped virus (CEV) or an extracellular enveloped virus (EEV) (SMITH et al. (2002), J. Gen. Virol., 83, 2915-2931).

As used throughout the entire application, "a" and "an" are used in the sense that they mean "at least one", "at least a first", "one or more" or "a plurality" of the referenced components or steps, unless the context clearly dictates otherwise.

As used throughout the entire application, "and/or" wherever used herein includes the meaning of "and", "or" and "all or any other combination of the elements connected by said term".

As used throughout the entire application, "comprising" and "comprise" are intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used throughout the entire application, "about" or "approximately" as used herein means within 20%, preferably within 10%, and more preferably within 5% of a given value or range.

The present invention relates to a method (i.e. Method A) for producing and purifying a wild type, an attenuated and/or a recombinant Orthopoxvirus, comprising the following steps:

a) preparing a culture of packaging cells;
b) infecting the packaging cell culture with an Orthopoxvirus;
c) culturing the infected packaging cells until progeny Orthopoxvirus is produced;
d) incubation in presence of one or more nucleases;
e) recovering the Orthopoxviruses from the culture supernatant and/or the packaging cells;
f) adding monovalent salts to the Orthopoxviruses recovered in step e) under suitable conditions to inhibit the nuclease(s) activity and to avoid the adsorption of said Orthopoxviruses to the anion exchange adsorbent in step g);
g) contacting the mixture obtained in step f) with an anion exchange adsorbent under suitable conditions to allow the capture of nucleic acids;
h) clarifying the mixture obtained in step g) under suitable conditions to allow the withdrawal of the cellular debris;
i) washing of the anion exchange adsorbent with a solution comprising monovalent salts under suitable conditions to recover the remained Orthopoxviruses in the flow through;

j) concentrating the flow through obtained in step h) and the flow through obtained in step i);

k) diafiltrating the fraction comprising the Orthopoxviruses obtained in step j).

According to a preferred embodiment, the method according to the invention is free from animal products (except the packaging cells). As used throughout the entire application, <<animal products>> refer to any compound or collection of compounds that was produced in or by an animal cell in a living organism.

According to a preferred embodiment, the method according to the invention is suitable for an aseptic industrial-scale manufacturing process to ensure a full compliance with regulatory requirements regarding sterility of vaccines.

As used throughout the entire application, “attenuated Orthopoxvirus” refers to any Orthopoxvirus that has been modified so that its pathogenicity in the intended subject is substantially reduced. Preferably, the Orthopoxvirus is attenuated to the point it is nonpathogenic from a clinical standpoint, i.e. that subjects exposed to the Orthopoxvirus do not exhibit a statistically significant increased level of pathology relative to control subjects. According to a preferred embodiment of the invention, the attenuated Orthopoxvirus is an attenuated VV or an attenuated MVA.

As used throughout the entire application, “recombinant Orthopoxvirus” refers to an Orthopoxvirus comprising an exogenous sequence inserted in its genome. As used herein, an exogenous sequence refers to a nucleic acid which is not naturally present in the parent virus.

As used throughout the entire application, “packaging cells” refers to a cell which can be infected by the Orthopoxvirus to be produced. The packaging cell may be a primary cell, a recombinant cell and/or a cell line. For example, a recombinant cell which contains the elements necessary for the production of a recombinant virus which are lacking in a recombinant viral vector can be used.

According to a preferred embodiment of the invention, the packaging cells are immortalized cell lines. As used throughout the entire application, “immortalized cell lines” refer to cell lines that proliferate in culture beyong the Hayflick limit.

According to the invention, the immortalized cell lines are preferably obtained from an avian cell belonging to the Anatidae family or the Phasianidae family. Among Anatidae, cell belonging to the *Cairina* or *Anas* genus is particularly preferred. Even more preferably, the immortalized avian cell lines belong to the *Cairina moschata* or to the *Anas platyrhynchos* species.

According to a more preferred embodiment of the invention, the packaging cells are immortalized avian cell lines obtained from an avian cell belonging to the Anatidae family, and preferably from *Cairina moschata* specie.

Preferred *Cairina moschata* immortalized avian cell lines according to the invention, are *Cairina moschata* immortalized avian cell lines comprising a nucleic acid sequence coding a telomerase reverse transcriptase (TERT) covered by patent application WO 2007/077256. Are particularly preferred, the following immortalized avian cell lines:

T3-17490 as deposited at the European Collection of Cell Cultures (ECACC) under accession number 08060502 (see FIGS. 2, 3 and 4) or a derivative thereof;

T6-17490 as deposited at the European Collection of Cell Cultures (ECACC) under accession number 08060501 (see FIGS. 5, 6 and 7) or a derivative thereof.

Other preferred *Cairina moschata* immortalized avian cell lines according to the invention, are *Cairina moschata* immortalized avian cell lines comprising an E1A nucleic acid sequence and a nucleic acid sequence coding a telomerase reverse transcriptase (TERT) covered by patent application WO 2009/004016.

As used throughout the entire application, “derivative” of the deposited immortalized avian cell lines refers to an immortalized avian cell line which comprises a nucleic acid sequence coding a “substance of interest”. As used herein, a “substance of interest” can include, but is not limited to, a pharmaceutically active protein e.g. growth factors, growth regulators, antibodies, antigens, their derivatives useful for immunization or vaccination and the like, interleukins, insulin, erythropoietin, G-CSF, GM-CSF, hPG-CSF, M-CSF, interferons (interferon-alpha, interferon-beta, interferon-gamma), blood clotting factors (e.g. Factor VIII; Factor IX; tPA) or combinations thereof.

Other immortalized cell lines that may be used in the method of the present invention are:

DF1 cell line covered by U.S. Pat. No. 5,879,924, which is a spontaneously immortalized chicken cell line derived from 10 day old East Lansing Line (ELL-0) eggs;

Ebx chicken cell line covered by patent application WO 2005/007840, which derives from embryonic stem cells by progressive severance from growth factors and feeder layer;

DEC 99 cell line (Ivanov et al. Experimental Pathology and Parasitology, 4/2000 Bulgarian Academy of Sciences), which is duck embryo permanent cell line.

According to another preferred embodiment of the invention, the packaging cells are primary cells. As used throughout the entire application, “primary cells” refer to cells that have been freshly isolated from an animal or human tissue, organ or organism, wherein the cells are not able to continuously and indefinitely replicate and divide. Usually, primary cells divide in cell culture less than 100 times, often less than 50 times, often less than 25 times. Primary cells have therefore not undergone an immortalized event. Primary cells include but are not limited to animal fibroblasts or cord blood lymphocytes.

According to a more preferred embodiment of the invention, the packaging cells are primary or secondary avian cells, and preferably chicken embryo fibroblasts (CEFs).

According to the present invention, the culture medium used for the preparation of the culture of packaging cells (i.e. during step a)), the culture medium used for the infection of said cell culture with an Orthopoxvirus (i.e. during step b)) and the culture medium used for the cultivation of said infected packaging cells (i.e. during step c)) can be the same or different.

According to a preferred embodiment, the cell culture media used according to the invention are free from animal product. Many media free from animal product have been already described and some of them are commercially available. For example 293 SFM II; 293-F Cells, SFM Adapted; 293-H Cells, SFM Adapted; 293Fectin™ Transfection Reagent; CD 293 AGT™; CD 293 Medium; FreeStyle™ 293 Expression System; FreeStyle™ 293 Medium; FreeStyle™ 293-F Cells, SFM Adapted; Adenovirus Expression Medium (AEM) Growth Medium for PER.C6® Cells; CD 293 AGT™; CD 293 Medium; COS-7L Cells, SFM Adapted; EPISERF® Medium; OptiPro™ SFM; VP-SFM; VP-SFM AGT™. (all available from Invitrogen) can be used as cell culture media in the process according to the invention. Cell culture media free from animal product used according to the invention can also be home-made media.

Step a) of preparation of a culture of packaging cells is well known to the one skilled in the art.

When the packaging cells are immortalized cell lines, said immortalized cell lines are cultured in the appropriate culture media. The methods may comprise growth adhering to surfaces, growth in suspension in presence or not of (micro) carriers, or combinations thereof. Culturing can be done for instance in dishes, roller bottles or in bioreactors, using batch, fed-batch, continuous systems, hollow fiber, and the like. In order to achieve large scale production of virus through cell culture it is preferred in the art to have cells capable of growing in suspension in presence or not of (micro)carriers, and it is preferred to have cells capable of being cultured in media free from animal product. Cell culture media used according to the invention are preferably free from animal product. Many media free from animal product has been already described and some of them are commercially available as previously described.

When the packaging cells are CEFs, said CEFs are preferably extracted from Specific Pathogen Free (SPF) eggs. SPF eggs are commercially available, for example from Charles River Laboratories (Wilmington, Mass., USA). Said eggs are preferably more than 9 days old, more preferably between 10 and 14 days old and even more preferably are 12 days old. Before the extraction of the embryo, the egg is preferably disinfected. Many methods and products dedicated to the disinfection of eggs are available in the prior art. Incubation in a formol solution (e.g. 2% formol, 1 min.) followed by a rinsing in 70% ethanol is particularly preferred. The cells of the embryos are then dissociated and purified. According to a preferred embodiment of the invention, the cells of the embryos are subjected to an enzymatic digestion step that allows the destruction of the intercellular matrix. For this purpose, the use of enzymes able to digest the intercellular matrix is particularly useful. Preferred enzyme according to the invention include but are not limited to Trypsin, Collagenase, Pronase, Dispase, Hyaluronidase and Neuraminidase. The enzymes used for the preparation of CEFs according to the invention are preferably of recombinant origin. The enzymes can be used alone or in combination. In a preferred embodiment of the invention dispase and tryspsin (e.g. TrypLE select from Gibco™) are used in combination. The one skilled in the art is able to determine the enzyme concentration, the temperature and the length of incubation allowing an efficient separation of the cells. The preparation of the CEFs culture can further include a filtration step and/or a centrifugation step in order to remove contaminants. According to the invention, the primary CEFs obtained can also either be used directly or after one further cell passage as secondary CEFs. The CEFs (i.e. primary or secondary) are then cultivated in an appropriate cell culture medium. Cell culture media used according to the invention are preferably free from animal product. Many media free from animal product has been already described and some of them are commercially available as previously described. According to the present invention, the CEFs are preferably cultivated in VP-SFM cell culture medium (Invitrogen). The CEFs are preferably cultivated for between 1 and 5 days, more preferably between 1 and 2 days and even more preferably 2 days before infection. The CEFs are preferably cultivated at a temperature comprised between 30° C. and 36.5° C.

Step b) of infection of the packaging cell culture (prepared in step a)) with an Orthopoxvirus is well known to the one skilled in the art. As used throughout the entire application, "infection" refers to the transfer of the viral nucleic acid to a cell, wherein the viral nucleic acid is replicated, viral proteins are synthesized, or new viral particles assembled. The one skilled in the art is able to select the most appropriate packaging cell for the production of a specific virus. According to a preferred embodiment, the method according to the invention comprises the use of CEFs or an immortalized avian cell line covered by patent application W0 2007/077256 or W0 2009/004016 for the production of an Orthopoxvirus, and preferably a MVA or a VV. Step b) of infection of the packaging cell culture (prepared in step a)) with an Orthopoxvirus is performed in an appropriate cell culture medium which can be the same or different from the cell culture medium used for the preparation of said packaging cell culture (i.e. during step a)). Cell culture media used according to the invention are preferably free from animal product. Many media free from animal product have been already described and some of them are commercially available as previously described. When the packaging cells are CEFs, step b) of infection of the CEFs culture is performed in Basal Medium Eagle cell culture medium (Invitrogen). The cell culture medium is preferably seeded with between between 0.5 to 1.5 and more preferably between 1.1 and 1.3 and even more preferably about 1.2 embryo/l of cell culture medium. In the specific embodiment where the Orthopoxvirus to produce is MVA, the MVA is seeded in the cell culture vessel at a MOI which is preferably comprised between 0.001 and 0.1, more preferably between 0.03 and 0.07 and even more preferably about 0.05. In another specific embodiment where the Orthopoxvirus to produce is VV, the VV is seeded in the cell culture vessel at a MOI which is preferably comprised between 0.0011 and 0.1, and more preferably about 0.0001.

Step c) of culture of the infected packaging cells (from step b)) until progeny Orthopoxvirus is produced, is well known to the one skilled in the art.

When the packaging cells are CEFs, step c) of culture of the infected CEFs is performed in an appropriate cell culture medium which can be the same or different from the cell culture medium used for the preparation of said CEFs culture (i.e. during step a) and from the cell culture medium used for the infection of said CEFs culture with an Orthopoxvirus (i.e. during step b)). Cell culture media used according to the invention are preferably free from animal product. Many media free from animal product have been already described and some of them are commercially available as previously described. According to the present invention, the culture of the infected CEFs is performed in Basal Medium Eagle cell culture medium (Invitrogen). The infected CEFs are preferably cultivated for between 1 and 6 days, more preferably between 2 and 4 days and even more preferably 3 days. The infected CEFs are preferably cultivated at a temperature which is lower than 37° C., preferably between 30° C. and 36.5° C.

Step d) of incubation in presence of one or more nucleases (i.e. endonuclease or exonucleases) is performed in order to degrade the nucleic acids (e.g. DNA; RNA) present in solution. Nucleases preferably used according to the present invention are endonucleases. Endonucleases can be classified based on their substrates as follows: deoxyribonucleases (DNases) which degrade DNA; ribonucleases (RNases) which degrade RNA; and endonucleases that degrade DNA and RNA. Endonucleases DNases include but are not limited to DNase I, DNase II and endodeoxyribonuclease IV. Endonucleases RNases include but are not limited to RNase I, RNase III, RNAse E, RNAse F and RNAse P. Endonucleases that degrade DNA and RNA include but are not limited to Benzonase®. In a preferred embodiment of the invention, step d) of incubating the Orthopoxviruses produced in step c)

is performed in presence of Benzonase®. Benzonase® degrades nucleic acid (e.g. DNA; RNA) by hydrolyzing internal phosphodiester bonds between specific nucleotides. Upon complete digestion, all free nucleic acids (e.g. DNA; RNA) present in solution are reduced to 5'-monophosphate terminated oligonucleotides which are 3 to 8 bases in length. Benzonaze® has no proteolytic activity. Benzonaze® used according to the present invention is preferably pharmaceutically acceptable. Pharmaceutically acceptable Benzonaze® are commercially available (e.g. Eurogentec under the reference ME-0280-10; Merck under the reference e.g. 1.01653.0001).

Preferred conditions for the action of nuclease(s) according to the invention are (as described in Example 1):

a pH comprised between 7.0 and 9.0, preferably between 7.5 and 8.5, and more preferably a pH of 8.0;

a concentration of cofactors selected from $Mg^{2+}$ and $Mn^{2+}$, preferably $Mg^{2+}$, in a range of 1 to 2 mM, and preferably 2 mM.

According to a preferred embodiment of the invention, the nuclease(s) is(are) incubated at a temperature comprised between 22° C. and 28° C., preferably at a temperature comprised between 23° C. and 27° C., more preferably at a temperature comprised between 24° C. and 26° C., and even more preferably at a temperature of 25° C. (as described in Example 1). In this present embodiment, the duration of step d) is preferably comprised between 1 and 5 hours, and more preferably 2 hours (as described in Example 1).

According to another preferred embodiment of the invention, the nuclease(s) is(are) incubated at a temperature comprised between 2° C. and 8° C., preferably at a temperature comprised between 3° C. and 7° C., more preferably at a temperature comprised between 4° C. and 6° C., and even more preferably at a temperature of 5° C. In this other embodiment, the duration of step d) is preferably comprised between 10 and 20 hours, and more preferably 18 hours.

According to the invention, the concentration of nuclease(s) used in step d) is in a range of 5 to 100 U/ml, preferably in a range of 5 to 50 U/ml, and more preferably 10 U/ml. As showed in FIG. 1, the use under the same conditions of 10 U/ml Benzonase® leads surprisingly to an equivalent decrease of DNA concentration after 2 hours of treatment (temperature of 25° C.; 2 mM $Mg^{2+}$; pH 8) compared with the use of 50 U/ml Benzonase®.

According to a preferred embodiment of the invention, step d) further comprises the addition of one or more detergents. Detergents include but are not limited to Tween, Triton X-100 (nonaethylene glycol octyl phenol ether), saponin, SDS, Brij 96, Polido-canol, N-octyl β-D-glucopyranoside and sodium carbonate. Preferred detergent used in step d) is Tween. Tween include but is not limited to Tween 20 (Polyoxyethylene Sorbitan Monolaurate), Tween 80 (Polyoxyethylene Sorbitan Monooleate) and Tween 85 (Polyoxyethylene Sorbitan Trioleate). Preferred Tween used in step d) is Tween 80. According to the invention, the concentration of detergent(s) used in step d) is in a range of 10 to 100 μg/L, preferably in a range of 10 to 55 μg/L.

The Orthopoxviruses produced and previously treated by nuclease(s) are then recovered from the culture supernatant and/or the packaging cells.

When the Orthopoxviruses are recovered from the packaging cells (i.e. from the packaging cells only, or from the packaging cells and from the supernatant), step e) can be preceded by a step allowing the disruption of the packaging cell membrane. This step leads to the liberation of the Orthopoxviruses from the packaging cells. The disruption of the packaging cell membrane can be induced by various techniques well known by the one skilled in the art. These techniques comprise but are not limited to freeze/thaw, hypotonic lysis, sonication (by using a sonicator) and microfluidization (by using a microfluidizer). Sonicators are commercially available from e.g. Heraeus PSP, Biologics, Misonix or GlenMills. Preferred sonicators used according to the present invention are SONITUBE 20 kHz type SM 20-120-3, SONITUBE 36 kHz type SM 35/3WU and SONITUBE 35 kHz type SM 35-400-3 (Heraeus PSP). Microfluidizers are commercially available from e.g. Microfluidics Corporation. The packaging cell membrane can also be disrupted by using a using a SLM Aminco French press. The packaging cell membrane can also be disrupted by using a high speed homogenizer. High speed homogenizers are commercially available from e.g. Silverson Machines or Ika-Labotechnik. Preferred high speed homogeneizer used according to the present invention is a SILVERSON L4R (Silverson Machines). The mixture obtained after disruption of the packaging cell membrane can further be incubated during at least 1 hour under agitation in order to allow the degradation by the nuclease(s) previously added (in step d)) of the nucleic acids (e.g. DNA) released from the packaging cells. In a specific embodiment of the invention, step e) is therefore preceded by:

1. a step allowing the disruption of the packaging cell membrane, preferably by using a high speed homogenizer or by sonication; and
2. a step of incubation of the mixture obtained in step 1) during at least 1 hour allowing the degradation by the nuclease(s) added in step d) of the nucleic acids (e.g. DNA) released from the packaging cells.

According to the invention, the duration of step 2) is preferably comprised between 1 and 5 hours, and more preferably 2 hours (as described in Example 1).

According to the invention, the nuclease(s) (previously added (in step d)) is(are) incubated during step 2) at a temperature comprised between 22° C. and 28° C., preferably at a temperature comprised between 23° C. and 27° C., more preferably at a temperature comprised between 24° C. and 26° C., and even more preferably at a temperature of 25° C. (as described in Example 1).

Step f) of addition of monovalent salts to the Orthopoxviruses recovered in step e) allows under suitable conditions:

to inhibit the nuclease(s) activity; and to avoid the adsorption of the Orthopoxviruses to the anion exchange adsorbent in step g), i.e. to avoid the adsorption of more than 10% of Orthopoxviruses to the anion exchange adsorbent. Therefore nucleic acids (e.g. DNA) only will be adsorbed to the anion exchange adsorbent in step g).

Monovalent salts include but are not limited to NaCl and KCl. Preferred monovalent salts used in step f) are NaCl. According to the invention, the concentration of monovalent salts in step f) is in a range of 200 to 300 mM, and preferably 250 mM or 300 mM. According to the invention, step f) is performed at a pH comprised between 7.0 and 9.0, preferably between 7.5 and 8.5, and more preferably at a pH of 8.0. According to the invention, step f) of addition of monovalent salts to the Orthopoxviruses recovered in step e) is preferably performed according to conditions described in Example 1, wherein NaCl 250 mM, or more preferably 300 mM, at pH 8.0 is used.

Step g) of contact the mixture obtained in step f) with an anion exchange adsorbent allows under suitable conditions the capture of nucleic acids (e.g. DNA) contained in said mixture. The Orthopoxviruses are not captured by the anion exchange adsorbent due to the treatment performed in step f).

According to the invention, step g) is performed at a pH comprised between 7.0 and 9.0, preferably between 7.5 and 8.5, and more preferably at a pH of 8.0 (as described in Example 1).

According to the invention, the duration of step g) is preferably comprised between 1 and 3 hours, and is more preferably 1 hour (as described in Example 1).

According to the invention, the functional groups of the anion exchange adsorbent used in step g) are primary, secondary, tertiary and quaternary amino group such as for instance dimethylaminoethyl (DMAE), diethylaminoethyl (DEAE), trimethylaminoethyl (TMAE), triethylaminoethyl (TEAE), the group —R—CH(OH)—$CH_2$—N+—$(CH_3)_3$ (also named Q group; see Streamline® resins, Pharmacia) and other groups such as for instance polyethyleneimine (PEI) that already have or will have a formal positive charge within the pH range of 7.0 to 9.0. Preferred functional groups of the anion exchange adsorbent used in step g) are selected from the group consisting of dimethylaminoethyl (DMAE), diethylaminoethyl (DEAE), trimethylaminoethyl (TMAE) and triethylaminoethyl (TEAE), and are more preferably trimethylaminoethyl (TMAE).

The anion exchange adsorbent used in step g) can consist in e.g. a beads-formed matrix or a membrane.

According to a preferred embodiment of the invention, the anion exchange adsorbent used in step g) consists in a beads-formed matrix. Matrix can be e.g. agarose, hydrophilic polymer, cellulose, dextran or silica. Chains (e.g. dextran chains) are coupled to the matrix. Functional groups as previously described are attached to the chains through chemically stable bonds (e.g. ether bonds). Preferred functional groups of the beads-formed matrix are trimethylaminoethyl (TMAE). According to the invention, the beads of the beads-formed matrix have a diameter higher than the pore size of filters used for the clarification step h). The beads of the beads-formed matrix have therefore preferably a diameter higher than 8 μm, more preferably a diameter comprised between 50 μm and 150 μm, more preferably a diameter comprised between 90 μm and 120 μm, and even more preferably a diameter of 120 μm. Based on the present characteristic of the invention, the Orthopoxviruses (having a diameter of 200-300 nm) will pass through the pore size of filters during the clarification step h) (i.e. the Orthopoxviruses will be recovered in the flow through). Anion exchange adsorbents consisting in beads-formed matrix used according to the invention are preferably autoclavable. Autoclavable anion exchange adsorbents consisting in beads-formed matrix have already been described and some of them are commercially available such as for instance UNOsphere® Q (BioRad), UNOsphere® S (BioRad), STREAMLINE™ Q Sepharose® XL (Amersham Biosciences), STREAMLINE™ SP Sepharose® XL (Amersham Biosciences) or BioSepra® Q hyperZ (Pall Corporation). Preferred autoclavable anion exchange adsorbent consisting in a beads-formed matrix according to the present invention is UNOsphere® (BioRad). UNOsphere® Q (BioRad) consists in hydrophilic spherical polymeric beads having a diameter of 120 μm and earring trimethylaminoethyl (TMAE) functional groups. Step g) of contact the mixture obtained in step f) with an anion exchange adsorbent wherein said exchange adsorbent consists in a beads-formed matrix is preferably performed according to the conditions described in Example 1, wherein UNOsphere® Q (BioRad) is used.

According to another preferred embodiment of the invention, the anion exchange adsorbent used in step g) consists in a membrane. Functional groups of the membrane can be as previously described. Preferred functional groups of the membrane are trimethylaminoethyl (TMAE). According to the present invention, the membrane has a pore size higher than the diameter of Orthopoxviruses (i.e. 200 nm). The Orthopoxviruses will be therefore recovered in the flow through. With this regard, the membrane has according to the invention a pore size comprised between 1 and 5 μm, and preferably a pore size of 3 μm. Anion exchange adsorbents consisting in membranes used according to the invention are preferably autoclavable. Autoclavable anion exchange adsorbents consisting in membranes have already been described and some of them are commercially available such as for instance Sartobind® 75 Q (Sartorius), CUNO PolyNet™ Filters (e.g. PolyNet™ PB P010, P020, P030, P050) or CUNO Betapure™ Filters (e.g. Betapure™ Z13-020, Z13-030, Z13-050). Preferred autoclavable anion exchange adsorbent consisting in a membrane according to the present invention is Sartobind® 75 Q (Sartorius).

When step g) is performed with an anion exchange adsorbent being a membrane, the following step h) of clarification (allowing the withdrawal of the cellular debris) is not required. The cellular debris have been retained by membranes having a pore size comprised between 1 and 5 μm, and preferably a pore size of 3 μm.

Step h) of clarification of the mixture obtained in step g) allows under suitable conditions the withdrawal of the cellular debris. According to the invention, the clarification of step h) is preferably performed by depth filtration. Depth filtration includes but is not limited to the use of one or more commercially available products such as Sartopure® filters from Sartorius (e.g. Sartopure® PP2), CUNO Incorporated AP series depth filters (e.g. AP01), CUNO Incorporated CP series depth filters (e.g. CP10, CP30, CP50, CP60, CP70, CP90), CUNO Incorporated HP series depth filters (e.g. HP10, HP30, HP50, HP60, HP70, HP90), CUNO Incorporated Calif. series depth filters (e.g. CA10, CA30, CA50, CA60, CA70, CA90), CUNO Incorporated SP series depth filters (e.g. SP10, SP30, SP50, SP60, SP70, SP90), CUNO Delipid and Delipid Plus filters, Millipore Corporation CE series depth filters (e.g. CE15, CE20, CE25, CE30, CE35, CE40, CE45, CE50, CE70, CE75), Millipore Corporation DE series depth filters (e.g. DE25, DE30, DE35, DE40, DE45, DE50, DE55, DE560, DE65, DE70, DE75), Millipore Corporation HC filters (e.g. A1HC, B1HC, COHC), CUNO PolyNet™ Filters (e.g. PolyNet™ PB P050, P100, P200, P300, P400, P500, P700), Millipore Clarigard and Polygard filters, CUNO Life Assure filters, ManCel Associates depth filters (e.g. PR 12 UP, PR12, PR 5 UP); and PALL or SeitzSchenk Incorporated filters. In order to improve the clarification capacity of the available depth filtration units, it can be useful to couple two or more units with decreasing pore sizes. In this embodiment, the mixture to be clarified passes through the first depth filtration unit where the biggest contaminants are retained and subsequently passes through the second depth filtration unit. With this regard, according to a preferred embodiment of the invention, the clarification of step h) is performed by depth filtration, preferably over filters having a pore size of 8 μm coupled to filters having a pore size of 5 μm. Preferred filters having a pore size of 8 μm and 5 μm used according to the present invention are Sartopure® filters commercially available from Sartorius (Sartopure® PP2). The depth filtration may be performed at a flow rate of at least 1 L/minute, and preferably at a flow rate of 1 L/minute. According to the invention, step h) is performed at a pH comprised between 7.0 and 9.0, preferably between 7.5 and 8.5, and more preferably at a pH of 8.0. Step h) of clarification of the mixture obtained in step g) is preferably performed according to conditions described in Example 1, wherein the clarification is performed by depth filtration over filters having a pore size of 8 μm coupled to filters having a pore size of 5 μm, and at a flow rate of 1 L/minute.

The Orthopoxviruses (having a diameter of 200-300 nm) pass through the pore size of filters during the clarification step h). The Orthopoxviruses are therefore recovered in the flow through.

Step i) of washing of the anion exchange adsorbent with a solution comprising monovalent salts allows under suitable conditions to recover the remained Orthopoxviruses in the flow through. Monovalent salts used include but are not limited to NaCl and KCl. Preferred monovalent salts used in step i) are NaCl. According to the invention, the concentration of monovalent salts used in step i) is in a range of 200 to 300 mM, and preferably 250 mM or 300 mM. According to the invention, step i) is performed at a pH comprised between 7.0 and 9.0, preferably between 7.5 and 8.5, and more preferably at a pH of 8.0. According to a preferred embodiment of the invention, the solution comprising monovalent salts in step i) is a pharmaceutically acceptable solution comprising 100 mM Tris-HCl, sucrose 5% (w/v), 10 mM sodium glutamate and 50 mM NaCl, pH 8.0 with physiological osmolarity (290 mOsm/kg) (i.e. SO8 buffer).

According to other preferred embodiments of the invention, the solution comprising monovalent salts in step i) is a pharmaceutically acceptable solution comprising for instance a Tris buffer, a triethanolamine buffer or a phosphate buffer. Step i) of washing of the anion exchange adsorbent with a solution comprising monovalent salts is preferably performed according to the conditions described in Example 1, wherein the washing is performed with SO8 pharmaceutically acceptable buffer comprising NaCl 250 mM, or more preferably 300 mM.

Step j) of concentration of the flow through obtained in step h) and the flow through obtained in step i) allows the elimination of the proteins present in said flow through fractions.

In a preferred embodiment of the invention, the concentration step j) is performed by microfiltration. Microfiltration is a pressure driven membrane process that concentrates and purifies large molecules. More specifically, a solution is passed through filters whose pore size has been chosen to reject the Orthopoxviruses in the retentate and allow small molecules (e.g. proteins) to pass through the filters into the permeate. Microfiltration reduces the volume of the extraction solution. With this regard, the microfiltration is therefore performed by using filters having a pore size lower than 0.2 μm, preferably a pore size comprised between 0.09 and 0.15 μm, and more preferably a pore size of 0.1 μm. Filters used according to the invention are preferably autoclavable. Autoclavable filters used in step j) are commercially available such as for instance Prostak Microfiltration Modules (Millipore) wherein Prostak Microfiltration Module PSVVAG021, PSVVAG041 and SK2P12E1 are preferred. Step j) of concentration of the flow through obtained in step h) and the flow through obtained in step i) is preferably performed according to the conditions described in Example 1, wherein the concentration is performed by microfiltration over filters having a pore size of 0.1 μm.

In another preferred embodiment of the invention, the concentration step j) is performed by ultrafiltration. According to the invention, the ultrafiltration is preferably a cross-flow filtration. The principle of cross-flow filtration is known to the person skilled in the art (see e.g. Richards, G. P. and Goldmintz, D., J. Virol. Methods (1982), 4 (3), pages 147-153. "Evaluation of a cross-flow filtration technique for extraction of polioviruses from inoculated oyster tissue homogenates").

Step k) of diafiltration of the fraction comprising the Orthopoxviruses obtained in step j) (e.g. the retentate when the concentration step k) has been performed by microfiltration or by ultrafiltration) is an improvement of microfiltration and involves diluting said fraction comprising the Orthopoxviruses with a solution to effect a reduction in the concentration of the impurities in said fraction. The dilution of the fraction comprising the Orthopoxviruses allows washing out more of the impurities from said fraction. It is understood that the diafiltration may be carried out in a batch mode, semi-continuous mode, or a continuous mode. The diafiltration step k) can be advantageously used to change the buffer in which the Orthopoxvirus is comprised. For example, it can be useful to exchange the buffer used in the purification process against a pharmaceutically acceptable buffer. According to the invention, the microfiltration is performed by using filters having a pore size lower than 0.2 μm, preferably a pore size comprised between 0.09 and 0.15 μm, and more preferably a pore size of 0.1 μm. Filters used according to the invention are preferably autoclavable. Autoclavable filters used in step k) are commercially available such as for instance Prostak Microfiltration Modules (Millipore) wherein Prostak Microfiltration Module PSVVAG021, PSVVAG041 and SK2P12E1 are preferred. Step k) of diafiltration of the fraction comprising the Orthopoxviruses obtained in step j) is preferably performed according to the conditions described in Example 1, wherein the diafiltration is performed over filters having a pore size of 0.1 μm.

Step j) of concentration and step k) of diafiltration can advantageously be done with the same type of filters.

The present method A of the invention can further comprise:

1. a step of gel filtration (i.e. step l)); and
2. a step of diafiltration (i.e. step m)).

Gel filtration step (i.e. step l): According to the invention, the sample obtained in step k) is treated on a solid support comprising beads having a diameter comprised between 3 and 160 μm, advantageously between 80 and 160 μm, preferably between 40 and 105 μm, more preferably between 25 and 75 μm, more preferably between 20 and 80 μm, and even more preferably between 20 and 60 μm. According to the invention, said support has a porosity closed to the diameter of the Orthopoxvirus (i.e. 200-300 nm) so that the latter does not penetrate into the beads. On the other hand, the molecules which are smaller in size penetrate into the beads and the migration thereof is slowed. The supports used in step l) of gel filtration can be based e.g. on agarose, dextran, acrylamide, silica, ethylene glycol/methacrylate copolymers, or mixtures thereof such as for instance mixtures of agarose and dextran. According to the invention, the supports are preferably used without functional groups. Gel filtration chromatography supports are commercially available such as for instance:

Ethylene glycol/methacrylate gel filtration chromatography supports (e.g. Toyopearl® HW 55, Toyopearl® HW 65 and Toyopearl® HW 75, having a bead diameter comprised between 20 and 60 μm, Tosohaas);

Allyl dextran/methylene bisacrylamide gel filtration chromatography supports (e.g. Sephacryl™ S300 HR having a bead diameter comprised between 25 and 75 μm; Sephacryl™ S400 HR having a bead diameter comprised between 25 and 75 μm; Sephacryl™ S500 HR having a bead diameter comprised between 25 and 75 μm; Sephacryl™ S1000 SF having a bead diameter comprised between 40 and 105 μm, all from Pharmacia);

N-acrylaminohydroxypropanediol gel filtration chromatography supports (e.g. Trisacryl having a bead diameter comprised between 80 and 160 μm, Biosepra);

Agarose gel filtration chromatography supports (e.g. Macro-Prep SE having a bead diameter comprised between 20 and 80 μm, Bio-Rad).

Ethylene glycol/methacrylate gel filtration chromatography supports (e.g. Toyopearl® HW 55, Toyopearl® HW 65 and Toyopearl® HW 75, having a bead diameter comprised between 20 and 60 μm, Tosohaas) are preferred.

Preferred conditions for step l) of gel filtration according to the invention are:

a concentration of monovalent salts selected from NaCl and KCl, preferably NaCl, in a range of 200 mM to 2 M, preferably in a range of 200 mM to 1 M, and more preferably at 500 mM;

a pH comprised between 7.0 and 9.0, preferably between 7.5 and 8.5, and more preferably a pH of 8.0.

The step m) of diafiltration is performed by means and conditions as previously described in step k) of diafiltration.

According to the present invention, each step from step f) to step l) of Method A previously described can be preceded by a step of incubating of the sample comprising the Orthopoxviruses in presence of one or more stabilizers. As used herein, "stabilizers" refers to agents allowing the preservation of the Orthopoxviruses. Stabilizers include but are not limited to saccharides (e.g. sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, sorbitol, glycerol), amino acids (e.g. Gly; Leu; Lys; Arg; Asp; Val; Glu), detergents (e.g. Triton X-100; Tween such as for instance Tween 20, Tween 80 or Tween 85) and salts (e.g. NaCl; KCl). According to a preferred embodiment of the invention, the stabilizers used in this step of incubation are saccharides and more preferably saccharose. According to the invention, the concentration of saccharose used in this step of incubation is in a range of 25 to 100 g/L, and preferably is 50 g/L. According to the invention, the stabilizer(s) can be comprised in a solution consisting of a pharmaceutically acceptable solution comprising 100 mM Tris-HCl, sucrose 5% (w/v), 10 mM sodium glutamate and 50 mM NaCl, pH 8.0 with physiological osmolarity (290 mOsm/kg) (i.e. SO8 buffer). According to the invention, the stabilizer(s) can be comprised in a solution consisting of a pharmaceutically acceptable solution comprising for instance a Tris buffer, a triethanolamine buffer or a phosphate buffer. According to the invention, this step of incubation in presence of stabilizers is performed at a pH comprised between 7.0 and 9.0, preferably between 7.5 and 8.5, and more preferably at a pH of 8.0. According to the invention, the duration of this step of incubation in presence of stabilizers is comprised between 1 hour and 20 hours, and more preferably 18 hours. According to the invention, this step of incubation in presence of stabilizers is performed at a temperature comprised between 2 and 8° C., preferably at a temperature comprised between 3° C. and 7° C., more preferably at a temperature comprised between 4° C. and 6° C., and even more preferably at a temperature of 5° C. This step of incubation in presence of stabilizers is preferably performed in presence of 50 g/L saccharose during 18 hours at a temperature of 5° C. as described in Example 1.

According to another embodiment of the Method A of the invention as previously described, the clarification step (step h)) is performed after the step e) of recovering the Orthopoxviruses from the culture supernatant and/or the packaging cells.

According to another embodiment of the invention, step f) of addition of monovalent salts to the Orthopoxviruses recovered in step e) under suitable conditions to inhibit the nuclease(s) activity and to avoid the adsorption of said Orthopoxviruses to the anion exchange adsorbent in step g), is not performed.

With this regard, the present invention therefore also relates to a method (i.e. Method B) for producing and purifying a wild type, an attenuated and/or a recombinant Orthopoxvirus, comprising the following steps:

a') preparing a culture of packaging cells;

b') infecting the packaging cell culture with an *Orthopoxvirus;* c') culturing the infected packaging cells until progeny Orthopoxvirus is produced;

d') incubation in presence of one or more nucleases;

e') recovering the Orthopoxviruses from the culture supernatant and/or the packaging cells;

f') incubating the Orthopoxviruses recovered in step e') in presence of:

1. one or more agents capable to inhibit the nuclease(s) activity, and optionally
2. one or more stabilizers.

g') contacting the mixture obtained in step f') with an anion exchange adsorbent under suitable conditions to allow the capture of the Orthopoxviruses and nucleic acids;

h') clarifying the mixture obtained in step g') under suitable conditions to allow the withdrawal of the cellular debris;

l') eluting the Orthopoxviruses with a solution comprising monovalent salts;

j') concentrating the mixture obtained in step i');

k') diafiltrating the fraction comprising the Orthopoxviruses obtained in step j').

Step a') of preparation of a culture of packaging cells refers to step a) of preparation of a culture of packaging cells as previously described.

Step b') of infection of the packaging cell culture with an Orthopoxvirus refers to step b) of infection of the packaging cell culture with an Orthopoxvirus as previously described.

Step c') of culture of the infected packaging cells until progeny Orthopoxvirus is produced refers to step c) of culture of the infected cells until progeny Orthopoxvirus is produced as previously described.

Step d') of incubation in presence of one or more nucleases refers to step d) of incubation in presence of one or more nucleases as previously described.

Step e') of recovering of the Orthopoxviruses from the culture supernatant and/or the packaging cells refers to step e) of recovering of the Orthopoxviruses from the culture supernatant and/or the packaging cells as previously described.

The Orthopoxviruses recovered in step e') are then incubated (step f')) in presence of:

1. one or more agents capable to inhibit the nuclease(s) activity, and optionally
2. one or more stabilizers.

Agents capable to inhibit the nuclease activity include but are not limited to chelating agents (e.g. ethylenediamine tetraacetate (EDTA); diethylenetriamine pentaacetate (DTPA); nitrilotriacetate (NTA)), monovalent salts (e.g. NaCl or KCl), proteases, phosphate, monovalent cations (e.g. $Na^+$; $Li^+$; $K^+$; $Ag^+$), guanidine hydrochloride and ammonium sulfate. Chelating agents such as e.g. EDTA, DTPA or NTA, remove metal ions (e.g. $Mg^{2+}$; $Mn^{2+}$) which constitute, as previoulsy described, essential cofactors for the activity of nuclease(s). Monovalent salts (e.g. NaCl or KCl) lead to the inactivation of nucleases at a concentration comprised between 50 and 150 mM, and preferably at about 100 mM. Phosphate and/or monovalent cations (e.g. $Na^+$; $Li^+$; $K^+$; $Ag^+$) lead to the inactivation of nucleases at a concentration of about or above 100 mM. Guanidine hydrochloride and ammonium sulfate lead to the inactivation of nucleases at a concentration above 100 mM. According to a preferred embodiment of the invention, the agents capable to inhibit the nuclease activity in step f') are chelating agents, and more preferably ethylenediamine tetraacetate (EDTA). According to the invention, the concentration of EDTA used in step f') is in a range of 5 to 20 mM, and preferably is 10 mM. According to another preferred embodiment of the invention, the agents capable to inhibit the nuclease activity in step f') are monovalent salts, preferably NaCl, and more preferably NaCl 100 mM. According to another preferred embodiment of the invention, the agents capable to inhibit the nuclease activity in step f') are monovalent salts and chelating agents, preferably NaCl and EDTA, and more preferably NaCl 100 mM and EDTA 10 mM (as described in Example 4).

According to the invention, step f') is performed at a pH comprised between 7.0 and 9.0, preferably between 7.5 and 8.5, and more preferably at a pH of 8.0 (as described in Example 4).

According to the invention, step f') is performed at a temperature comprised between 2° C. and 8° C., preferably at a temperature comprised between 3° C. and 7° C., more preferably at a temperature comprised between 4° C. and 6° C., and even more preferably at a temperature of 5° C. According to the invention, the duration of step f') is comprised between 5 minutes and 20 hours. In a preferred embodiment of the invention, the duration of step f') is comprised between 2 and 20 hours, and is preferably 18 hours. In this present embodiment, the Orthopoxviruses obtained in step e') are also incubated in presence of one or more stabilizers, in addition to agent(s) capable to inhibit the nuclease(s) activity (as previously described). "Stabilizers" refers in step f') to agents allowing the preservation of the Orthopoxviruses during the treatment with agent(s) capable to inhibit the nuclease(s) activity in said step f'). Stabilizers include but are not limited to saccharides (e.g. sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, sorbitol, glycerol), amino acids (e.g. Gly; Leu; Lys; Arg; Asp; Val; Glu), detergents (e.g. Triton X-100; Tween such as for instance Tween 20, Tween 80 or Tween 85) and salts (e.g. NaCl; KCl). According to a preferred embodiment of the invention, the stabilizers used in step f') are saccharides, and preferably saccharose. According to the invention, the concentration of saccharose used in step f') is in a range of 25 to 100 g/L, and preferably is 50 g/L. According to the invention, the stabilizer(s) can be comprised in a solution consisting of a pharmaceutically acceptable solution comprising 100 mM Tris-HCl, sucrose 5% (w/v), 10 mM sodium glutamate and 50 mM NaCl, pH 8.0 with physiological osmolarity (290 mOsm/kg) (i.e. SO8 buffer). According to the invention, the stabilizer(s) can be comprised in a solution consisting of a pharmaceutically acceptable solution comprising for instance a Tris buffer, a triethanolamine buffer or a phosphate buffer.

Step g') of contact of the mixture obtained in step f') with an anion exchange adsorbent allows under suitable conditions the capture of said Orthopoxvirus and nucleic acids (e.g. DNA) as well contained in said mixture.

According to the invention, step g') is performed at a pH comprised between 7.0 and 9.0, preferably between 7.5 and 8.5, and more preferably at a pH of 8.0 (as described in Example 4).

According to the invention, the duration of step g') is preferably comprised between 1 and 3 hours, and is more preferably 1 hour (as described in Example 4).

According to the invention, the functional groups of the anion exchange adsorbent used in step g') are primary, secondary, tertiary and quaternary amino group such as for instance dimethylaminoethyl (DMAE), diethylaminoethyl (DEAE), trimethylaminoethyl (TMAE), triethylaminoethyl (TEAE), the group —R—CH(OH)—$CH_2$—N+—$(CH_3)_3$ (also named Q group; see Streamline® resins, Pharmacia) and other groups such as for instance polyethyleneimine (PEI) that already have or will have a formal positive charge within the pH range of 7.0 to 9.0. Preferred functional groups of the anion exchange adsorbent used in step g') are selected from the group consisting of dimethylaminoethyl (DMAE), diethylaminoethyl (DEAE), trimethylaminoethyl (TMAE) and triethylaminoethyl (TEAE), and are more preferably trimethylaminoethyl (TMAE).

The anion exchange adsorbent used in step g') can consist in e.g. a beads-formed matrix or a membrane.

According to a preferred embodiment of the invention, the anion exchange adsorbent used in step g') consists in a beads-formed matrix. Matrix can be e.g. agarose, hydrophilic polymer, cellulose, dextran or silica. Chains (e.g. dextran chains) are coupled to the matrix. Functional groups as previously described are attached to the chains through chemically stable bonds (e.g. ether bonds). Preferred functional groups of the beads-formed matrix are trimethylaminoethyl (TMAE). According to the invention, the beads of the beads-formed matrix have a diameter higher than the pore size of filters used for the clarification step h'). The beads of the beads-formed matrix have therefore preferably a diameter higher than 8 μm, more preferably a diameter comprised between 50 μm and 150 μm, more preferably a diameter comprised between 90 μm and 120 μm, and even more preferably a diameter of 120 μm. Based on the present characteristic of the invention, the beads of the beads-formed matrix caring the Orthopoxviruses will be retained by the filters during the clarification step h') as well as the cellular debris. Anion exchange adsorbents consisting in beads-formed matrix used according to the invention are preferably autoclavable. Autoclavable anion exchange adsorbents consisting in beads-formed matrix have already been described and some of them are commercially available such as for instance UNOsphere® 0 (BioRad), UNOsphere® S (BioRad), STREAMLINE™ Q Sepharose® XL (Amersham Biosciences), STREAMLINE™ SP Sepharose® XL (Amersham Biosciences) or BioSepra® hyperZ (Pall Corporation). Preferred autoclavable anion exchange adsorbent consisting in a beads-formed matrix according to the present invention is UNOsphere® (BioRad) and BioSepra® Q hyperZ (Pall Corporation). UNOsphere® Q (BioRad) consists in hydrophilic spherical polymeric beads having a diameter of 120 μm and carring trimethylaminoethyl (TMAE) functional groups. BioSepra® Q hyperZ (Pall Corporation) consists in highly dense and porous zirconium dioxide beads having a diameter of about 75 μm and carring quaternary amine Q functional groups. Step g') of contact the mixture obtained in step f') with an anion exchange adsorbent wherein said exchange adsorbent consists in a beads-formed matrix is preferably performed according to the conditions described in Example 4, wherein BioSepra® Q hyperZ (Pall Corporation) is used.

According to another preferred embodiment of the invention, the anion exchange adsorbent used in step g') consists in a membrane. Functional groups of the membrane can be as previously described. Preferred functional groups of the membrane are trimethylaminoethyl (TMAE). According to a preferred embodiment of the invention, the membrane used in step g') has a pore size comprised between 1 and 5 μm, and preferably a pore size of 3 μm. According to another preferred embodiment of the invention, the membrane used in step g') has a pore size lower than the size of Orthopoxviruses (i.e. 200 nm), and more particularly a pore size of 0.1 μm. Many anion exchange adsorbents consisting in membranes have already been described and some of them are commercially available such as for instance Sartobind® 75 Q (Sartorius). Anion exchange adsorbents consisting in membranes used according to the invention are preferably autoclavable. Autoclavable anion exchange adsorbents consisting in membranes have already been described and some of them are commercially available such as for instance Sartobind® 75 Q (Sartorius). Preferred autoclavable anion exchange adsorbent consisting in a membrane according to the present invention is Sartobind® 75 Q (Sartorius).

When step g') is performed with an anion exchange adsorbent being an anion exchange membrane, the following step h') of clarification (allowing the withdrawal of the cellular debris) is not required. The cellular debris have been retained by anion exchange membranes (as previously described) used in step f').

Step h') of clarification of the mixture obtained in step g') refers to step h) of clarification of the mixture obtained in step g) as previously described.

According to a preferred embodiment of the invention, when step g') is performed with an anion exchange adsorbent being a beads-formed matrix, step h') can be preceded by a step allowing the removal of said beads-formed matrix caring the Orthopoxviruses. With this regard, said step is performed by using e.g. filter bags having therefore a pore size lower than the size of the beads beads-formed matrix. According to the invention, the pore size of the filter bags is comprised between 10 and 100 μm, preferably between 25 and 100 μm, and more preferably 50 μm. Filter bags used according to the invention are preferably autoclavable. Autoclavable filter bags have already been described and some of them are commercially available such as for instance CUNO™ Felt Filter Bags (CUNO) wherein polyester Felt Filter Bags (e.g. NB EES 0010, 0025, 0050, 0100), polyester/polypropylene Felt Filter Bags (e.g. NB PES 0010, 0025, 0050, 0100) and nylon monofilament Felt Filter Bags (e.g. NB NYS 0025, 0050, 0100) are preferred.

Step i') of elution of the Orthopoxviruses with a solution comprising monovalent salts allows the recovering of the captured Orthopoxviruses from the anion exchange adsorbent. Monovalent salts used include but are not limited to NaCl and KCl. Preferred monovalent salts used in step i') are NaCl. According to one embodiment of the invention, the elution is performed by an increasing monovalent salts concentration gradient, ranging preferably from of 0 to 2.5 M, more preferably from of 0 to 2 M and even more preferably from of 0 to 1.5 M. According to another embodiment of the invention, the elution is performed by a single-step elution at a concentration of monovalent salts which is below 1M, preferably comprised between 300 mM and 750 mM, and more preferably of 500 mM. According to the invention, step i') is performed at a pH comprised between 7.0 and 9.0, preferably between 7.5 and 8.5, and more preferably at a pH of 8.0. According to a preferred embodiment of the invention, the solution comprising monovalent salts in step i') is a pharmaceutically acceptable solution comprising 100 mM Tris-HCl, sucrose 5% (w/v), 10 mM sodium glutamate and 50 mM NaCl, pH 8.0 with physiological osmolarity (290 mOsm/kg) (i.e. SO8 buffer). According to other preferred embodiments of the invention, the solution comprising monovalent salts in step i') is a pharmaceutically acceptable solution comprising for instance a Tris buffer, a triethanolamine buffer or a phosphate buffer. Step i') of elution of the Orthopoxviruses with a solution comprising monovalent salts is preferably performed according to the conditions described in Example 4, wherein the elution is performed by an increasing NaCl concentration gradient (300 mM; 400 mM; 500 mM) in SO8 buffer.

Step j') of concentration of the mixture obtained in step i') allows the elimination of the proteins present in said flow through fractions.

In a preferred embodiment of the invention, the concentration step j') is performed by microfiltration (as previously described in step j)).

In another preferred embodiment of the invention, the concentration step j') is performed by ultrafiltration (as previously described in step j)).

Step k') of diafiltration of the fraction comprising the Orthopoxviruses obtained in step j') refers to step k) of diafiltrating the fraction comprising the Orthopoxviruses obtained in step j) as previously described.

The present method B of the invention can further comprise:

1. a step of gel filtration (i.e. step l')); and
2. a step of diafiltration (i.e. step m')).

Step l') of gel filtration refers to step l) of gel filtration.

Step m') of diafiltration refers to step m) of diafiltration.

According to the present invention, each step from step f') to step l') of the Method B previously described may be preceded by a step of incubating of the sample comprising the Orthopoxviruses in presence of one or more stabilizers. As used herein, "stabilizers" refers to agents allowing the preservation of the Orthopoxviruses. Stabilizers include but are not limited to saccharides (e.g. sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, sorbitol, glycerol), amino acids (e.g. Gly; Leu; Lys; Arg; Asp; Val; Glu), detergents (e.g. Triton X-100; Tween such as for instance Tween 20, Tween 80 or Tween 85) and salts (e.g. NaCl; KCl). According to a preferred embodiment of the invention, the stabilizers used in this step of incubation are saccharides and more preferably saccharose. According to the invention, the concentration of saccharose used in this step of incubation is in a range of 25 to 100 g/L, and preferably is 50 g/L. According to the invention, the stabilizer(s) can be comprised in a solution consisting of a pharmaceutically acceptable solution comprising 100 mM Tris-HCl, sucrose 5% (w/v), 10 mM sodium glutamate and 50 mM NaCl, pH 8.0 with physiological osmolarity (290 mOsm/kg) (i.e. SO8 buffer). According to the invention, the stabilizer(s) can be comprised in a solution consisting of a pharmaceutically acceptable solution comprising for instance a Tris buffer, a triethanolamine buffer or a phosphate buffer. According to the invention, this step of incubation in presence of stabilizers is performed at a pH comprised between 7.0 and 9.0, preferably between 7.5 and 8.5, and more preferably at a pH of 8.0. According to the invention, the duration of this step of incubation in presence of stabilizers is comprised between 1 hour and 20 hours, and more preferably 18 hours. According to the invention, this step of incubation in presence of stabilizers is performed at a temperature comprised between 2° C. and 8° C., preferably at a temperature comprised between 3° C. and 7° C., more preferably at a temperature comprised between 4° C. and 6° C., and even more preferably at a temperature of 5° C. This step of incubation in presence of stabilizers is preferably performed in presence of 50 g/L saccharose during 18 hours at a temperature of 5° C.

According to another embodiment of the Method B of the invention as previously described, the clarification step (step h')) is performed after the step e') of recovering the Orthopoxviruses from the culture supernantant and/or the packaging cells.

The present invention also related to methods that combine step(s) of Method A and step(s) of Method B, as previously described.

With this regard, the present invention more particularly relates to a method (i.e. Method C) for producing and purifying a wild type, an attenuated and/or a recombinant Orthopoxvirus, comprising the following steps:

a") preparing a culture of packaging cells;

b") infecting the packaging cell culture with an *Orthopoxvirus;* c") culturing the infected packaging cells until progeny Orthopoxvirus is produced;

d") incubation in presence of one or more nucleases;

e") recovering the Orthopoxviruses from the culture supernatant and/or the packaging cells;

f") incubating the Orthopoxviruses recovered in step e") in presence of:

1. one or more agents capable to inhibit the nuclease(s) activity, and optionally
2. one or more stabilizers;

g") contacting the mixture obtained in step f") with an anion exchange adsorbent under suitable conditions to allow the capture of said Orthopoxviruses and nucleic acids;

h") clarifying the mixture obtained in step g") under suitable conditions to allow the withdrawal of the cellular debris;

i") eluting the Orthopoxviruses with a solution comprising monovalent salts;

j") adding monovalent salts to the Orthopoxviruses eluted in step i") in order to avoid the adsorption of said Orthopoxviruses to the anion exchange adsorbent in step k");

k") contacting the mixture obtained in step j") with an anion exchange adsorbent under suitable conditions to allow the capture of nucleic acids;

l") washing of the anion exchange adsorbent with a solution comprising monovalent salts under suitable conditions to recover the remained Orthopoxviruses in the flow through;

m") concentrating the flow through obtained in step l");

n") diafiltrating the fraction comprising the Orthopoxviruses obtained in step m").

Step a") of preparation of a culture of packaging cells refers to step a) of preparation of a culture of packaging cells as previously described.

Step b") of infection of the packaging cell culture with an Orthopoxvirus refers to step b) of infection of the packaging cell culture with an Orthopoxvirus as previously described.

Step c") of culture of the infected packaging cells until progeny Orthopoxvirus is produced refers to step c) of culture of the infected cells until progeny Orthopoxvirus is produced as previously described.

Step d") of incubation in presence of one or more nucleases refers to step d) of incubation in presence of one or more nucleases as previously described.

Step e") of recovering of the Orthopoxviruses from the culture supernatant and/or the packaging cells refers to step e) of recovering of the Orthopoxviruses from the culture supernatant and/or the packaging cells as previously described.

Step f") of incubation of the Orthopoxviruses recovered in step e") in presence of (1) one or more agents capable to inhibit the nuclease(s) activity, and optionally (2) one or more stabilizers, refers to step f') of incubation of the Orthopoxviruses recovered in step e') in presence of (1) one or more agents capable to inhibit the nuclease(s) activity, and optionally (2) one or more stabilizers, as previously described.

Step g") of contact the mixture obtained in step f") with an anion exchange adsorbent under suitable conditions to allow the capture of said Orthopoxviruses and nucleic acids, refers to step g') of contact the mixture obtained in step f') with an anion exchange adsorbent under suitable conditions to allow the capture of said Orthopoxviruses and nucleic acids, as previously described.

Step h") of clarification of the mixture obtained in step g") refers to step h) of clarification of the mixture obtained in step g) as previously described.

Step i") of elution of the Orthopoxviruses with a solution comprising monovalent salts refers to step i') of elution of the Orthopoxviruses with a solution comprising monovalent salts as previously described.

Step j") of addition of monovalent salts to the Orthopoxviruses previously eluted in step i") allows under suitable conconditions to avoid the adsorption of said Orthopoxviruses to the anion exchange adsorbent in step k") (i.e. to avoid the adsorption of more than 10% of Orthopoxviruses to the anion exchange adsorbent). Therefore nucleic acids (e.g. DNA) only will be adsorbed to the anion exchange adsorbent in step k"). Monovalent salts include but are not limited to NaCl and KCl. Preferred monovalent salts used in step j") are NaCl. According to the invention, the concentration of monovalent salts in step j") is in a range of 200 to 300 mM, and preferably 250 mM or 300 mM. According to the invention, step j") is performed at a pH comprised between 7.0 and 9.0, preferably between 7.5 and 8.5, and more preferably at a pH of 8.0.

Step k") of contact of the mixture obtained in step j") with an anion exchange adsorbent under suitable conditions to allow the capture of nucleic acids, refers to step g) of contact of the mixture obtained in step f) with an anion exchange adsorbent under suitable conditions to allow the capture of nucleic acids as previously described.

Step l") of washing of the anion exchange adsorbent with a solution comprising monovalent salts under suitable conditions to recover the remained Orthopoxviruses in the flow through, refers to step i) of washing of the anion exchange adsorbent with a solution comprising monovalent salts under suitable conditions to recover the remained Orthopoxviruses in the flow through as previously described.

Step m") of concentration of the flow through obtained in step l") allows the elimination of the proteins present in said flow through fraction. In a preferred embodiment of the invention, the concentration step m") is performed by microfiltration (as previously described in step j)). In another preferred embodiment of the invention, the concentration step m") is performed by ultrafiltration (as previously described in step j)).

Step n") of diafiltration of the fraction comprising the Orthopoxviruses obtained in step m") refers to step k) of diafiltrating the fraction comprising the Orthopoxviruses obtained in step j) as previously described.

The present method C of the invention can further comprise:

1. a step of gel filtration (i.e. step o")); and
2. a step of diafiltration (i.e. step p")).

Step o") of gel filtration refers to step l) of gel filtration.

Step p") of diafiltration refers to step m) of diafiltration.

According to the present invention, each step from step f") to step p") (and preferably each step from step k") to step p")) of the Method C previously described may be preceded by a step of incubating of the sample comprising the Orthopoxviruses in presence of one or more stabilizers. As used herein, "stabilizers" refers to agents allowing the preservation of the Orthopoxviruses. Stabilizers include but are not limited to saccharides (e.g. sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, sorbitol, glycerol), amino acids (e.g. Gly; Leu; Lys; Arg; Asp; Val; Glu), detergents (e.g. Triton X-100; Tween such as for instance Tween 20, Tween 80 or Tween 85) and salts (e.g. NaCl; KCl). According to a preferred embodiment of the invention, the stabilizers used in this step of incubation are saccharides and more preferably saccharose. According to the invention, the concentration of saccharose used in this step of incubation is in a range of 25 to 100 g/L, and preferably is 50 g/L. According to the invention, the stabilizer(s) can be comprised in a solution consisting of a pharmaceutically acceptable solution comprising 100 mM Tris-HCl, sucrose 5% (w/v), 10 mM sodium glutamate and 50 mM NaCl, pH 8.0 with physiological osmolarity (290 mOsm/kg) (i.e. SO8 buffer). According to the invention, the stabilizer(s) can be comprised in a solution consisting of a pharmaceutically acceptable solution comprising for instance a Tris buffer, a triethanolamine buffer or a phosphate buffer. According to the invention, this step of incubation in presence of stabilizers is performed at a pH comprised between 7.0 and 9.0, preferably between 7.5 and 8.5, and more preferably at a pH of 8.0. According to the invention, the duration of this step of incubation in presence of stabilizers is comprised between 1 hour and 20 hours, and more preferably 18 hours. According to the invention, this step of incubation in presence of stabilizers is performed at a temperature comprised between 2° C. and 8° C., preferably at a temperature comprised between 3° C. and 7° C., more preferably at a temperature comprised between 4° C. and 6° C., and even more preferably at a temperature of 5° C. This step of incubation in presence of stabilizers is preferably performed in presence of 50 g/L saccharose during 18 hours at a temperature of 5° C.

According to another embodiment of the Method C of the invention as previously described, the clarification step (step h")) is performed after the step e") of recovering the Orthopoxviruses from the culture supernantant and/or the packaging cells.

According to the present invention, the samples comprising the Orthopoxviruses obtained after each step of the methods of the present invention may be preserved by freezing well known from those skilled in the art.

According to the invention, the methods of the present invention are performed at a pH comprised between 7.0 and 9.0, preferably between 7.5 and 8.5, and more preferably at a pH of 8.0.

In a preferred embodiment of the invention, the Orthopoxvirus is a Vaccinia Virus (VV). Preferred VV according to the invention are VV as described for instance in patent applications PCT/EP2008/009720 (WO2009/065546 describing VV comprising defective I4L and/or F4L gene(s)) or PCT/EP2008/009721 (WO2009/065547 describing VV comprising defective F2L gene).

In another preferred embodiment of the invention, the Orthopoxvirus is a modified Vaccinia Virus Ankara (MVA). Preferred MVA according to the present invention are MVA as deposited before Collection Nationale de Cultures de Microorganismes (CNCM) under depositary N° I-721, MVA 575 (ECACC V00120707) and MVA-BN (ECACC V00083008).

The term "recombinant Orthopoxvirus" refers to an Orthopoxvirus comprising an exogenous sequence inserted in its genome. As used herein, an exogenous sequence refers to a nucleic acid which is not naturally present in the parent Orthopoxvirus.

In one embodiment, the exogenous sequence encodes a molecule having a directly or indirectly cytotoxic function. By "directly or indirectly" cytotoxic, we mean that the molecule encoded by the exogenous sequence may itself be toxic (for example ricin, tumour necrosis factor (TNF), interleukin-2 (IL2), interferon-gamma (IFNγ), ribonuclease, deoxyribonuclease, *Pseudomonas* exotoxin A) or it may be metabolised to form a toxic product, or it may act on something else to form a toxic product. The sequence of ricin cDNA is disclosed in Lamb et al (Eur. J. Biochem., 1985, 148, 265-270).

In a preferred embodiment of the invention, the exogenous sequence is a suicide gene. A suicide gene encodes a protein able to convert a relatively non-toxic prodrug to a toxic drug. For example, the enzyme cytosine deaminase converts 5-fluorocytosine (5-FC) to 5-fluorouracil (5-FU) (Mullen et al (1922) PNAS 89, 33); the herpes simplex enzyme thymidine kinase sensitises cells to treatment with the antiviral agent ganciclovir (GCV) or aciclovir (Moolten (1986) Cancer Res. 46, 5276; Ezzedine et al (1991) New Biol 3, 608). The cytosine deaminase of any organism, for example *E. coli* or *Saccharomyces cerevisiae*, may be used. Thus, in preferred embodiment of the invention, the suicide gene encodes a protein having a cytosine deaminase activity, and more preferably FCU1 protein or FCU1-8 protein covered by patent applications WO 99/54481, WO 05/07857, PCT/EP2008/009720 and PCT/EP2008/009721 incorporated herein by reference.

With this regard, preferred recombinant Orthopoxviruses produced according to the method of the invention are:

- MVA-FCU1 (see WO 99/54481) also called TG4023;
- MVA-FCU1-8 (see WO 05/07857); and
- VV-FCU1 wherein said VV comprises more particularly a defective I4L and/or F4L gene, and a defective J2R gene (see PCT/EP2008/009720/WO2009/065546 and PCT/EP2008/009721/WO2009/065547).

Other examples of pro-drug/enzyme combinations include those disclosed by Bagshawe et al (WO 88/07378), namely various alkylating agents and the *Pseudomonas* spp. CPG2 enzyme, and those disclosed by Epenetos & Rowlinson-Busza (WO 91/11201), namely cyanogenic pro-drugs (for example amygdalin) and plant-derived beta-glucosidases. Enzymes that are useful in this embodiment of the invention include, but are not limited to, alkaline phosphatase useful for converting phosphate-containing prodrugs into free drugs; arylsulfatase useful for converting sulfate-containing prodrugs into free drugs; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs (Massey R. et al., Nature, 1987, 328, 457-458). Similarly, prodrugs include, but are not limited to, the above-listed prodrugs, e.g., phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted. Examples of cytotoxic drugs that can be derivatized into a prodrug form for use in this invention include, but are not limited to, etoposide, teniposide, adriamycin, daunomycin, carminomycin, aminopterin, dactinomycin, mitomycins, cis-platinum and cis-platinum analogues, bleomycins, esperamicins (see for example U.S. Pat. No. 4,675,187), 5-fluorouracil, melphalan and other related nitrogen mustards.

In a further embodiment the exogenous gene encodes a ribozyme capable of cleaving targeted RNA or DNA. The targeted RNA or DNA to be cleaved may be RNA or DNA which is essential to the function of the cell and cleavage thereof results in cell death or the RNA or DNA to be cleaved may be RNA or DNA which encodes an undesirable protein, for example an oncogene product, and cleavage of this RNA or DNA may prevent the cell from becoming cancerous.

In a still further embodiment the exogenous gene encodes an antisense RNA. By "antisense RNA" we mean an RNA molecule which hybridises to, and interferes with the expression from an mRNA molecule encoding a protein or to another RNA molecule within the cell such as pre-mRNA or tRNA or rRNA, or hybridises to, and interferes with the expression from a gene.

In another embodiment of the invention, the exogenous sequence replaces the function of a defective gene in the target cell. There are several thousand inherited genetic diseases of mammals, including humans, which are caused by defective genes. Examples of such genetic diseases include cystic fibrosis, where there is known to be a mutation in the CFTR gene; Duchenne muscular dystrophy, where there is known to be a mutation in the dystrophin gene; sickle cell disease, where there is known to be a mutation in the HbA gene. Many types of cancer are caused by defective genes, especially protooncogenes, and tumour-suppressor genes that have undergone mutation. Examples of protooncogenes are ras, src, bcl and so on; examples of tumour-suppressor genes are p53 and Rb.

In a further embodiment of the invention, the exogenous sequence encodes a Tumor Associated Antigen (TAA). TAA refers to a molecule that is detected at a higher frequency or density in tumor cells than in non-tumor cells of the same tissue type. Examples of TAA includes but are not limited to CEA, MART1, MAGE1, MAGES, GP-100, MUC1 (see WO 92/07000, WO 95/09241 and Rochlitz et al. J Gene Med. 2003 August; 5(8):690-9 incorporated herein by reference), MUC2, pointed mutated ras oncogene, normal or point mutated p53, overexpressed p53, CA-125, PSA, C-erb/B2, BRCA I, BRCA II, PSMA, tyrosinase, TRP1, TRP2, NY-ESO-1, TAG72, KSA, HER-2/neu, bcr-abl, pax3-fkhr, ews-fli-1, surviving and LRP. According to a more preferred embodiment the TAA is MUC1.

In another embodiment of the invention, the exogenous gene encodes an antigen. As used herein, "antigen" refers to a ligand that can be bound by an antibody; an antigen need not itself be immunogenic. Preferably the antigen is derived from a virus such as for example HIV-1, (such as gp 120 or gp 160), any of Feline Immunodeficiency virus, human or animal herpes viruses, such as gD or derivatives thereof or Immediate Early protein such as ICP27 from HSV1 or HSV2, cytomegalovirus (such as gB or derivatives thereof), Varicella Zoster Virus (such as gpI, II or III), or from a hepatitis virus such as hepatitis B virus (HBV) for example Hepatitis B Surface antigen or a derivative thereof, hepatitis A virus (HAV), hepatitis C virus (HCV; see WO 04/111082; preferentially non structural HCV protein from genotype 1b strain ja), and hepatitis E virus (HEV), or from other viral pathogens, such as Respiratory Syncytial Virus, Human Papilloma Virus (HPV; see WO 90/10459, WO 95/09241, WO 98/04705, WO 99/03885 WO 07/121894 and WO 07/121894; E6 and E7 protein from the HPV16 strain are preferred; see also Liu et al. Proc Natl Acad Sci USA. 2004 Oct. 5; 101 Suppl 2:14567-71) or Influenza virus, or derived from bacterial pathogens such as *Salmonella, Neisseria, Borrelia* (for example OspA or OspB or derivatives thereof), or *Chlamydia*, or *Bordetella* for example P.69, PT and FHA, or derived from parasites such as *plasmodium* or *Toxoplasma*. According to a more preferred embodiment the antigen is selected from HCV or HPV.

With this regard, preferred recombinant Orthopoxviruses produced according to the method of the invention is MVA-HCV (see WO 04/111082) also called TG4040.

The recombinant Orthopoxvirus can comprise more than one exogenous sequence and each exogenous sequence can encodes more than one molecule. For example, it can be useful to associate in a same recombinant Orthopoxvirus, an exogenous sequenced encoding e.g. a TAA (as previously described) or an antigen (as previously described) with an exogenous sequence encoding a cytokine (e.g. interleukin (IL as for instance IL2); tumour necrosis factor (TNF); interferon-(IFN); colony stimulating factor (CSF)). With this regard, preferred recombinant Orthopoxviruses produced according to the method of the invention are:

MVA-[MUC1-1L2] (see WO 92/07000 and WO 95/09241) also called TG4010; and

MVA-[HPV-IL2] (see WO 90/10459, WO 95/09241, WO 98/04705, WO 99/03885, WO 07/121894 and WO 07/121894) also called TG4001.

Advantageously, the recombinant Orthopoxvirus further comprises the elements necessary for the expression of the exogenous sequence(s). The elements necessary for the expression comprise of the set of elements allowing the transcription of a nucleotide sequence to RNA and the translation of a mRNA to a polypeptide, in particular the promoter sequences and/or regulatory sequences which are effective in the cell to be infected by the recombinant Orthopoxvirus of the invention, and optionally the sequences required to allow the excretion or the expression at the surface of the cells for said polypeptide. These elements may be inducible or constitutive. Of course, the promoter is adapted to the recombinant Orthopoxvirus selected and to the host cell. There may be mentioned, by way of example, the Vaccinia Virus promoters p7.5K pH5R, pK1L, p28, p11 or a combination of said promoters. The literature provides a large amount of information relating to such promoter sequences. The elements necessary can, in addition, include additional elements which improve the expression of the exogenous sequence or its maintenance in the host cell. There may be mentioned in particular the intron sequences (WO 94/29471), secretion signal sequences, nuclear localization sequences, internal sites for reinitiation of translation of the IRES type, poly A sequences for termination of transcription.

The present invention also relates to a purified wild type, attenuated and/or recombinant Orthopoxvirus obtained by the method of the present invention for use as a pharmaceutical composition, preferably as a vaccine.

As used herein, a "pharmaceutical composition" refers to a composition comprising a pharmaceutically acceptable carrier. Said pharmaceutically acceptable carrier is preferably isotonic, hypotonic or weakly hypertonic and has a relatively low ionic strength, such as for example a sucrose solution. Moreover, such a carrier may contain any solvent, or aqueous or partially aqueous liquid such as nonpyrogenic sterile water. The pH of the pharmaceutical composition is, in addition, adjusted and buffered so as to meet the requirements of use in vivo. The pharmaceutical compositions may also include a pharmaceutically acceptable diluent, adjuvant or excipient, as well as solubilizing, stabilizing and preserving agents. For injectable administration, a formulation in aqueous, non-aqueous or isotonic solution is preferred. It may be provided in a single dose or in a multidose in liquid or dry (powder, lyophilisate and the like) form which can be reconstituted at the time of use with an appropriate diluent.

The present invention also relates to a purified wild type, attenuated and/or recombinant Orthopoxvirus obtained by the method of the present invention for the treatment and/or the prevention a cancer, an infectious disease and/or an autoimmune disorder.

As used herein, "cancer" refers but is not limited to lung cancer (e.g. small cell lung carcinomas and non-small cell lung), bronchial cancer, oesophageal cancer, pharyngeal cancer, head and neck cancer (e.g. laryngeal cancer, lip cancer, nasal cavity and paranasal sinus cancer and throat cancer), oral cavity cancer (e.g. tongue cancer), gastric cancer (e.g. stomach cancer), intestinal cancer, gastrointestinal cancer, colon cancer, rectal cancer, colorectal cancer, anal cancer, liver cancer, pancreatic cancer, urinary tract cancer, bladder cancer, thyroid cancer, kidney cancer, carcinoma, adenocarcinoma, skin cancer (e.g. melanoma), eye cancer (e.g. retinoblastoma), brain cancer (e.g. glioma, medulloblastoma and cerebral astrocytoma), central nervous system cancer, lymphoma (e.g. cutaneous B-cell lymphoma, Burkitt's lymphoma, Hodgkin's syndrome and non-Hodgkin's lymphoma), bone cancer, leukaemia, breast cancer, genital tract cancer, cervical cancer (e.g. cervical intraepithelial neoplasia), uterine cancer (e.g. endometrial cancer), ovarian cancer, vaginal cancer, vulvar cancer, prostate cancer, testicular cancer. "Cancers" also refer to virus-induced tumors, including, but is not limited to papilloma virus-induced carcinoma, herpes virus-induced tumors, EBV-induced B-cell lymphoma, hepatitis B-induced tumors, HTLV-1-induced lymphoma and HTLV-2-induced lymphoma.

As used herein, "infectious disease" refers to any disease that is caused by an infectious organism. Infectious organisms include, but are not limited to, viruses (e.g. single stranded RNA viruses, single stranded DNA viruses, human immunodeficiency virus (HIV), hepatitis A, B, and C virus, herpes simplex virus (HSV), cytomegalovirus (CMV), respiratory syncytial virus (RSV), Epstein-Barr virus (EBV) or human papilloma virus (HPV)), parasites (e.g. protozoan and metazoan pathogens such as *Plasmodia* species, *Leishmania* species, *Schistosoma* species or *Trypanosoma* species), bacteria (e.g. *Mycobacteria* in particular, *M. tuberculosis, Salmonella, Streptococci, E. coli* or *Staphylococci*), fungi (e.g. *Candida* species or *Aspergillus* species), *Pneumocystis Carinii*, and prions.

As used herein, "autoimmune disorder" refers to two general types: 'Systemic autoimmune diseases' (i.e., disorders that damage many organs or tissues), and 'localized autoimmune diseases' (i.e., disorders that damage only a single organ or tissue). However, the effect of 'localized autoimmune diseases', can be systemic by indirectly affecting other body organs and systems. 'Systemic autoimmune diseases' include but are not limited to rheumatoid arthritis which can affect joints, and possibly lung and skin; lupus, including systemic lupus erythematosus (SLE), which can affect skin, joints, kidneys, heart, brain, red blood cells, as well as other tissues and organs; scleroderma, which can affect skin, intestine, and lungs; Sjogren's syndrome, which can affect salivary glands, tear glands, and joints; Goodpasture's syndrome, which can affect lungs and kidneys; Wegener's granulomatosis, which can affect sinuses, lungs, and kidneys; polymyalgia rheumatica, which can affect large muscle groups, and temporal arteritis/giant cell arteritis, which can affect arteries of the head and neck. 'Localized autoimmune diseases' include but are not limited to Type 1 Diabetes Mellitus, which affects pancreas islets; Hashimoto's thyroiditis and Graves' disease, which affect the thyroid; celiac disease, Crohn's diseases, and ulcerative colitis, which affect the gastrointestinal tract; multiple sclerosis (MS) and Guillain-Barre syndrome, which affect the central nervous system; Addison's disease, which affects the adrenal glands; primary biliary sclerosis, sclerosing cholangitis, and autoimmune hepatitis, which affect the liver; and Raynaud's phenomenon, which can affect the fingers, toes, nose, ears.

The present invention also relates to a pharmaceutical composition, preferably a vaccine, comprising a purified wild type, attenuated and/or recombinant Orthopoxvirus obtained by the method of the present invention. According to the invention, said pharmaceutical composition is intended for the treatment and/or the prevention a cancer, an infectious disease and/or an autoimmune disorder.

The present invention also relates to the use of a purified wild type, attenuated and/or recombinant Orthopoxvirus obtained by the method of the present invention for the preparation of a pharmaceutical composition, preferably a vaccine, for the treatment and/or the prevention a cancer, an infectious disease and/or an autoimmune disorder.

The pharmaceutical composition and in particular the vaccine may be manufactured conventionally for administration by the local, parenteral or digestive route. The routes of administration may be for instance the intragastric, subcutaneous, intracardiac, intramuscular, intravenous, intraperitoneal, intratumor, intranasal, intrapulmonary or intratracheal route. For the latter three embodiments, administration by aerosol or instillation is advantageous. The administration may be made as a single dose or repeated once or several times after a certain time interval. The appropriate route of administration and dosage vary as a function of various parameters, for example, of the individual, of the disease to be treated or of the gene(s) of interest to be transferred. According to a first possibility, the pharmaceutical composition and in particular the vaccine may be administered directly in vivo (for example by intravenous injection, into an accessible tumor or at its periphery, subcutaneously for a therapeutic or prophylactic vaccination). It is also possible to adopt the ex vivo approach which consists in collecting cells from the patient (bone marrow stem cells, peripheral blood lymphocytes, muscle cells and the like), transfecting or infecting them in vitro according to prior art techniques and readministering them to the patient. It is moreover possible to envisage, where appropriate and without departing from the scope of the present invention, carrying out simultaneous or successive administrations, by different routes, of the various components contained in the pharmaceutical composition and in particular in the vaccine.

The present invention also relates to the use of an immortalized avian cell line obtained from an avian cell belonging to the Anatidae family for the production of a wild type, attenuated and/or recombinant Orthopoxvirus according to the method of the invention. Among Anatidae, cell belonging to the *Cairina* or *Anas* genus is particularly preferred. Even more preferably, the immortalized avian cell lines belong to the *Cairina moschata* or to the *Anas platyrhynchos* species.

According to a preferred embodiment of the invention, *Cairina moschata* immortalized avian cell lines are *Cairina moschata* immortalized avian cell lines comprising a nucleic acid sequence coding a telomerase reverse transcriptase (TERT) covered by patent application WO 2007/077256. Are particularly preferred, the following immortalized avian cell lines:

T3-17490 as deposited at the European Collection of Cell Cultures (ECACC) under accession number 08060502 (see FIGS. 2, 3 and 4) or a derivative thereof;

T6-17490 as deposited at the European Collection of Cell Cultures (ECACC) under accession number 08060501 (see FIGS. 5, 6 and 7) or a derivative thereof.

With this regard, the present invention also relates to:

The use of a *Cairina moschata* immortalized avian cell line comprising a nucleic acid sequence coding a telomerase reverse transcriptase (TERT) for the production of a wild type, attenuated and/or recombinant Orthopoxvirus according to the method of the invention.

The use of T3-17490 *Cairina moschata* immortalized avian cell line as deposited at the European Collection of Cell Cultures (ECACC) under accession number 08060502 (as described in Example 2) or a derivative thereof for the production of a wild type, attenuated and/or recombinant Orthopoxvirus according to the method of the invention.

The use of T6-17490 *Cairina moschata* immortalized avian cell line as deposited at the European Collection of Cell Cultures (ECACC) under accession number 08060501 (as described in Example 3) or a derivative thereof for the production of a wild type, attenuated and/or recombinant Orthopoxvirus according to the method of the invention.

According to another preferred embodiment of the invention, *Cairina moschata* immortalized avian cell lines are *Cairina moschata* immortalized avian cell lines comprising an E1A nucleic acid sequence and a nucleic acid sequence coding a telomerase reverse transcriptase (TERT) covered by patent application WO 2009/004016.

With this regard, the present invention also relates to the use of a *Cairina moschata* immortalized avian cell line comprising an E1A nucleic acid sequence and a nucleic acid sequence coding a telomerase reverse transcriptase (TERT) for the production of a wild type, attenuated and/or recombinant Orthopoxvirus according to the method of the invention.

As used throughout the entire application, "derivative" of the deposited immortalized avian cell lines refers to an immortalized avian cell line which comprises a nucleic acid sequence coding a "substance of interest". As used herein, a "substance of interest" can include, but is not limited to, a pharmaceutically active protein e.g. growth factors, growth regulators, antibodies, antigens, their derivatives useful for immunization or vaccination and the like, interleukins, insulin, erythropoietin, G-CSF, GM-CSF, hPG-CSF, M-CSF, interferons (interferon-alpha, interferon-beta, interferon-gamma), blood clotting factors (e.g. Factor VIII; Factor IX; tPA) or combinations thereof.

Figure 1:
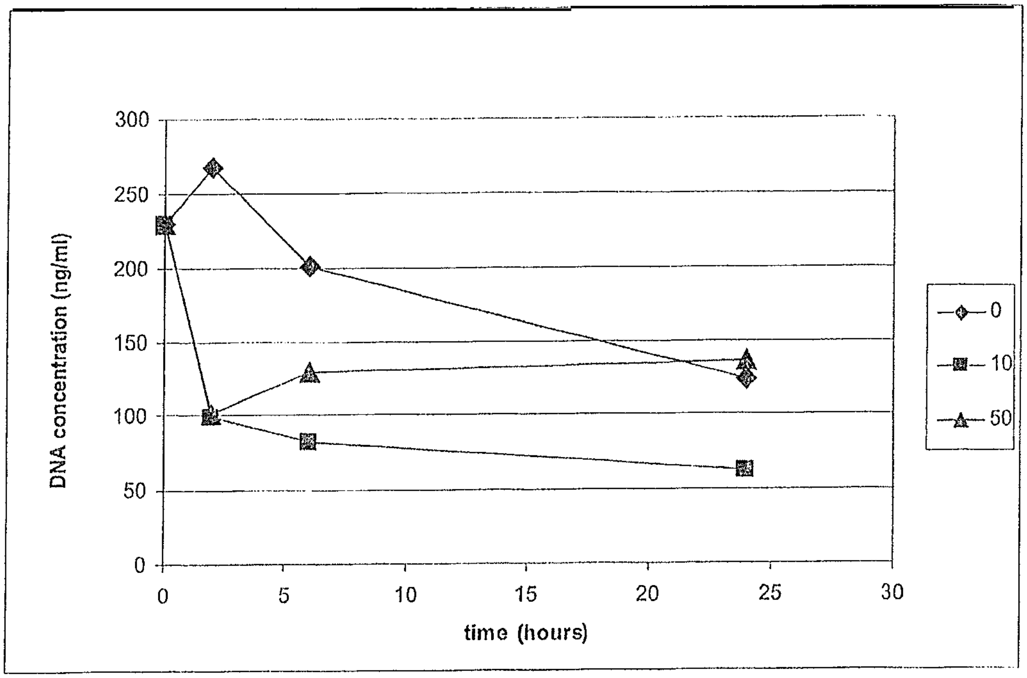
FIG. 1: depicts the effect of various Benzonase® concentrations (i.e. 10 mM; 50 mM) on Benzonase® endonuclease activity (temperature of 25° C.; $Mg^{2+}$ 2 mM; pH 8).

To illustrate the invention, the following examples are provided. The examples are not intended to limit the scope of the invention in any way.

EXAMPLES

Example 1

Methode A

Step a): Preparing a Culture of Packaging Cells.

Sixty six SPF eggs are incubated in for 60 secondes in a 2% formol solution. After being rinsed with 70% ethanol, the eggs are opened, the embryos are extracted and dissected. The obtained tissues are then digested at 36.5° C. for 120 minutes by dispase (UI/ml) and triple select (UI/ml). The mixture is filtrated to remove undigested tissues and the CEFs are collected by centrifugation (2300 rpm, 15 minutes). The CEFs are incubated in 55 L of VP-SFM (Invitrogen) for 2 days at 36.5° C.

Step b): Infecting the Packaging Cell Culture with an Orthopoxvirus.

The cell culture media is then discarded and the MVA-[MUC1-IL2] also called TG4010 (0.05 MOI) (MVA deposited before Collection Nationale de Cultures de Microorganismes (CNCM) under depositary N° I-721) is added in 55 L of Basal Medium Eagle (Invitrogen).

Step c): Culturing the Infected Packaging Cells until Progeny Orthopoxvirus is Produced.

The infected CEFs are then incubated for three days at 36.5° C.

Step d): Incubation in Presence of One or More Nucleases.

Infected CEFs comprising the MVA progeny are then incubated in presence of Benzonase® 10 U/ml or 50 U/ml (Merck; Reference 1.01653.0001) under the following conditions:

2 hours under agitation at a temperature of 25° C.;

$Mg^{2+}$ 2 mM;

pH of 8.0.

Step e): Recovering the Orthopoxviruses from the Culture Supernatant and/or the Packaging Cells.

The cell culture media and the CEFs are collected. The mixture is then homogenised for 15 minutes at 11 ml/min with a Silverson© L4R high speed homogeniser (Silverson), or for 75 minutes at 1500 ml/min with a SONITUBE 36 kHz type SM 35/3WU (Heraeus PSP).

The obtained mixture is then incubated 2 hours under agitation at a temperature of 25° C. and pH 8.0.

Step f): Adding Monovalent Salts to the Orthopoxviruses Recovered in Step e) Under Suitable Conditions to Inhibit the Nuclease(s) Activity and to Avoid the Adsorption of Said Orthopoxviruses to the Anion Exchange Adsorbent in Step g).

The obtained mixture is then incubated in presence of NaCl 250 mM and pH 8.0.

Step g): Contacting the Mixture Obtained in Step f) with an Anion Exchange Adsorbent Under Suitable Conditions to Allow the Capture of Nucleic Acids.

The obtained mixture is then added to UNOsphere® Q (BioRad). The UNOsphere® Q (BioRad) beads-formed matrix is first washed with sterile water, then autoclavated in Tris 10 mM buffer (pH 8.0), and then equilibrated with NaCl 250 mM or 300 mM buffer (pH 8.0).

The UNOsphere® Q (BioRad) beads-formed matrix is then added by using a peristaltic Watson-Marlow pump (Reference 323ES/4D, 520S; Watson-Marlow) to the mixture obtained in step f) contained in a Flexboy® bag (Reference FFB101961; Sartorius Stedim biotech).

The UNOsphere® Q (BioRad) beads-formed matrix and the mixture obtained in step f) are kept in contact during 1 hour under slow agitation at room temperature (20° C. to 22° C.).

Step h): Clarifying the Mixture Obtained in Step g) Under Suitable Conditions to Allow the Withdrawal of the Cellular Debris.

The obtained mixture is then clarified by depth filtration on a Sartopure® PP2 8 μm (Sartorius) coupled to a Sartopure® PP2 5 μm (Sartorius) at a flow rate of 1 L/minute.

Step i): Washing of the Anion Exchange Adsorbent with a Solution Comprising Monovalent Salts Under Suitable Conditions to Recover the Remained Orthopoxviruses in the Flow Through.

The UNOsphere® Q (BioRad) is then washed (v/v) with NaCl 250 mM or 300 mM in SO8 buffer (10 mM Tris-HCl; sucrose 5% (w/v); 10 mM sodium glutamate; 50 mM NaCl; pH 8.0 with physiological osmolarity (290 mOsm/kg)) by using a peristaltic Watson-Marlow pump (Reference 323ES/4D, 520S; Watson-Marlow).

The flow trough obtained in step h) and the flow trough obtained in step i) are then incubated overnight (i.e. 18 hours) at 5° C. in presence of saccharose 50 g/L final.

Step j): Concentrating the Flow Through Obtained in Step h) and the Flow Through Obtained in Step i).

The flow trough obtained in step h) and the flow trough obtained in step i) are then concentrated 18 times through a 0.1 μm Prostak Microfiltration Module (Reference PSVVAG021, Millipore).

Step k): Diafiltrating the Fraction Comprising the Orthopoxviruses Obtained in Step j).

The retentate is then diafiltred on the same module i.e. 0.1 μm Prostak Microfiltration Module (Reference PSVVAG021, Millipore).

The quantification of DNA is performed using Quant-iT™ Picogreen® dsDNA Assays Kit (Cat. No. P7589, Invitrogen).

Results: No remaining DNA is detected.

Example 2

Figure 2:
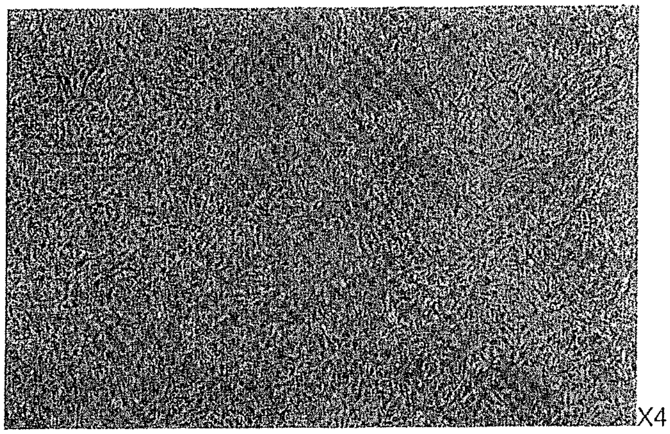
FIG. 2: depicts light microscopy imaging of T3-17490 (ECACC 08060502) *Cairina moschata* immortalized avian cell line (passage 39).
Figure 2:
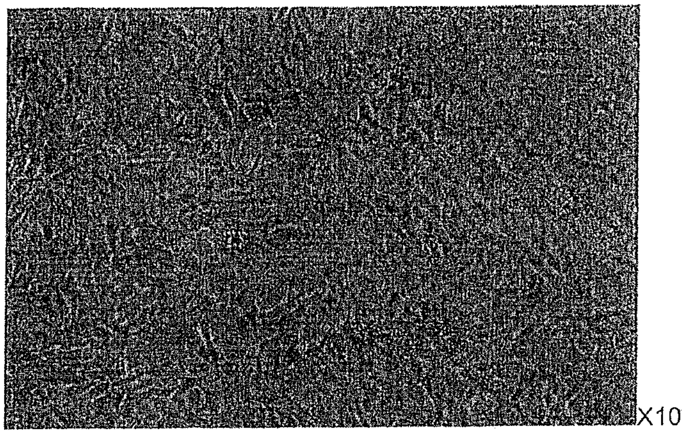
Figure 2:
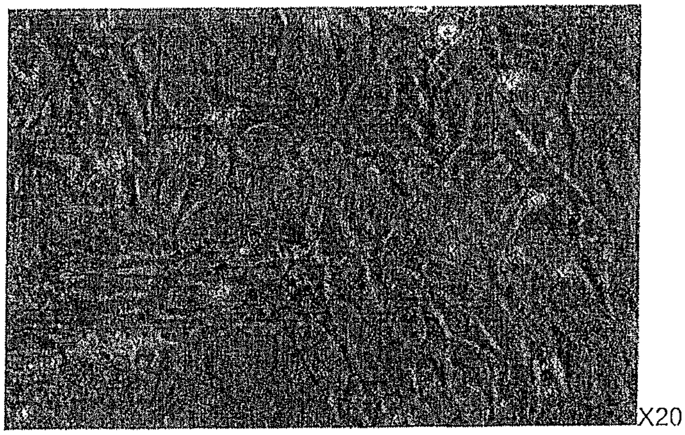
Figure 3:
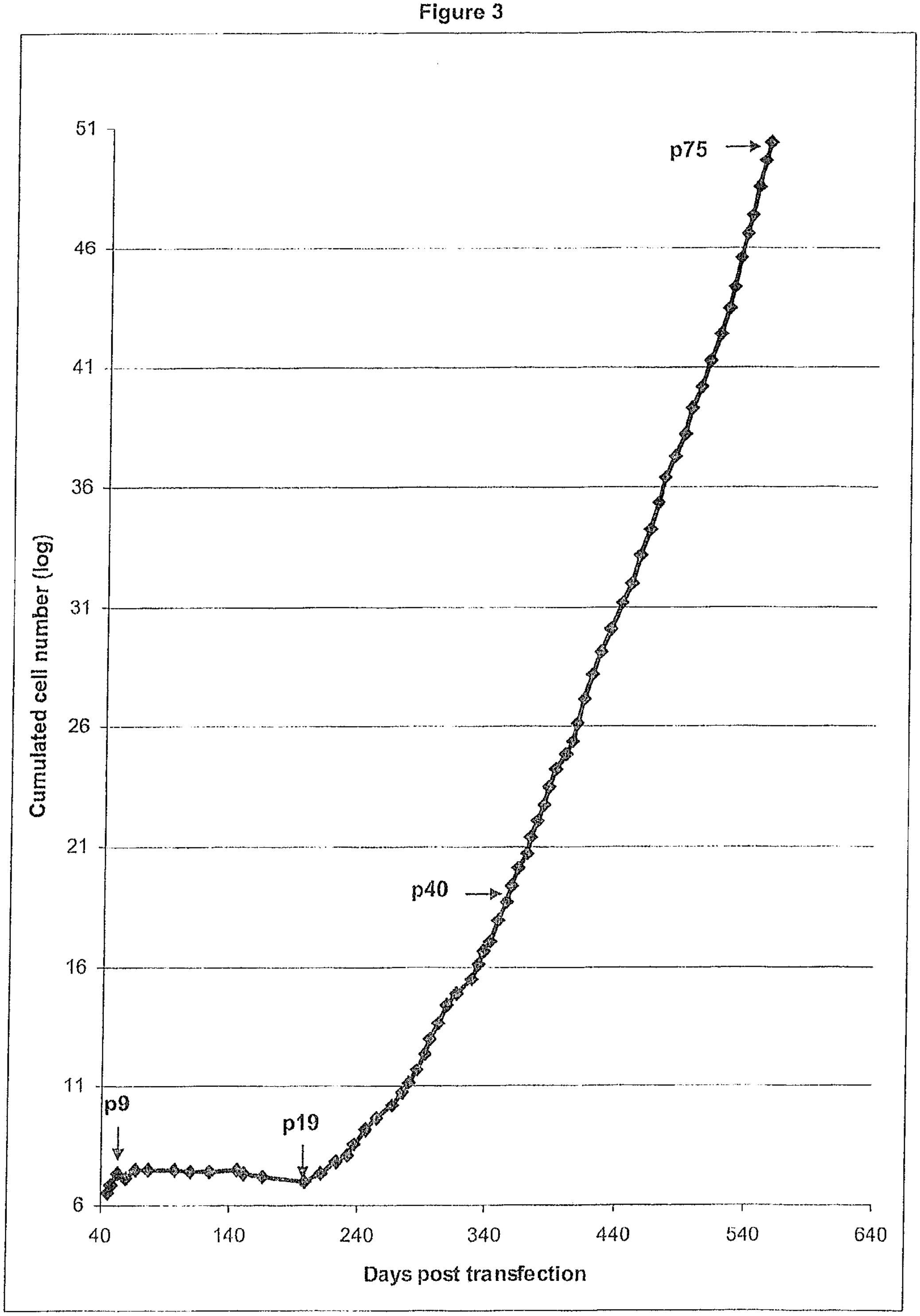
FIG. 3: despicts T3-17490 (ECACC 08060502) *Cairina moschata* immortalized avian cell line growth curve (from passage 7 to passage 75).
Figure 4:
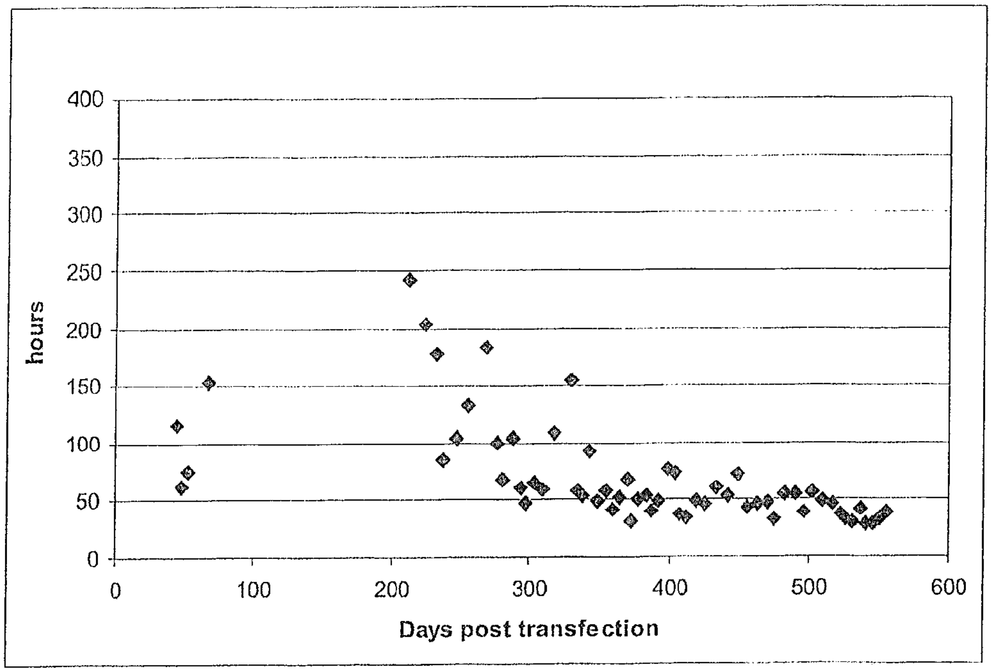
FIG. 4: depicts T3-17490 (ECACC 08060502) *Cairina moschata* immortalized avian cell line population doubling time evolution (from passage 7 to passage 75).

T3-17490 Immortalized *Cairina Moschata* Cell Line (as Deposited at ECACC Under Accession Number 08060502) Used for the Production of an Orthopoxvirus According to the Method of the Invention T3-17490 cells (passage 39) have a homogenous fibroblast like morphology (FIG. 2). The static monolayer is stable up to 100% confluence and subject to contact inhibition. The cells were tested negative for mycoplasma contamination and for microbial contamination as well. The T3-17490 cell line growth curve (from passage 7 to passage 75) (FIG. 3) shows a continuous exponential growth phase from passage 19 to passage 75. Focusing on the evolution of the population doubling time (PDT), a progressive stabilisation and decrease is observed, in particular it can be noted that the PDT is stabilised under the 48 h mark during the 10 latest passages (FIG. 4). The corresponding number of population doublings (population doubling level, PDL) has been calculated by cumulating the 2 exponential growth phases: during the 75 passages the cells have undergone at least 147 population doublings (PD). The number of population doublings a primary cell can undergo before entering senescence is tissue and specie dependent. It is commonly admitted that the upper limit is situated between 50 and 60 PD. The T3-17490 cells are therefore far beyond the Hayflick limit and are consequently referred as immortalized cell line.

N.B.:

The population doubling level (PDL) refers to the number of cell generations (biomass 2 fold increase). PDL calculation: PDL=Ln(final/initial cell number)/Ln(2);

The population doubling time (PDT), also called generation time, is the time needed for one population doubling. PDT calculation: PDT=Δt*Ln(2)/Ln(final/initial cell number).

Example 3

Figure 5:
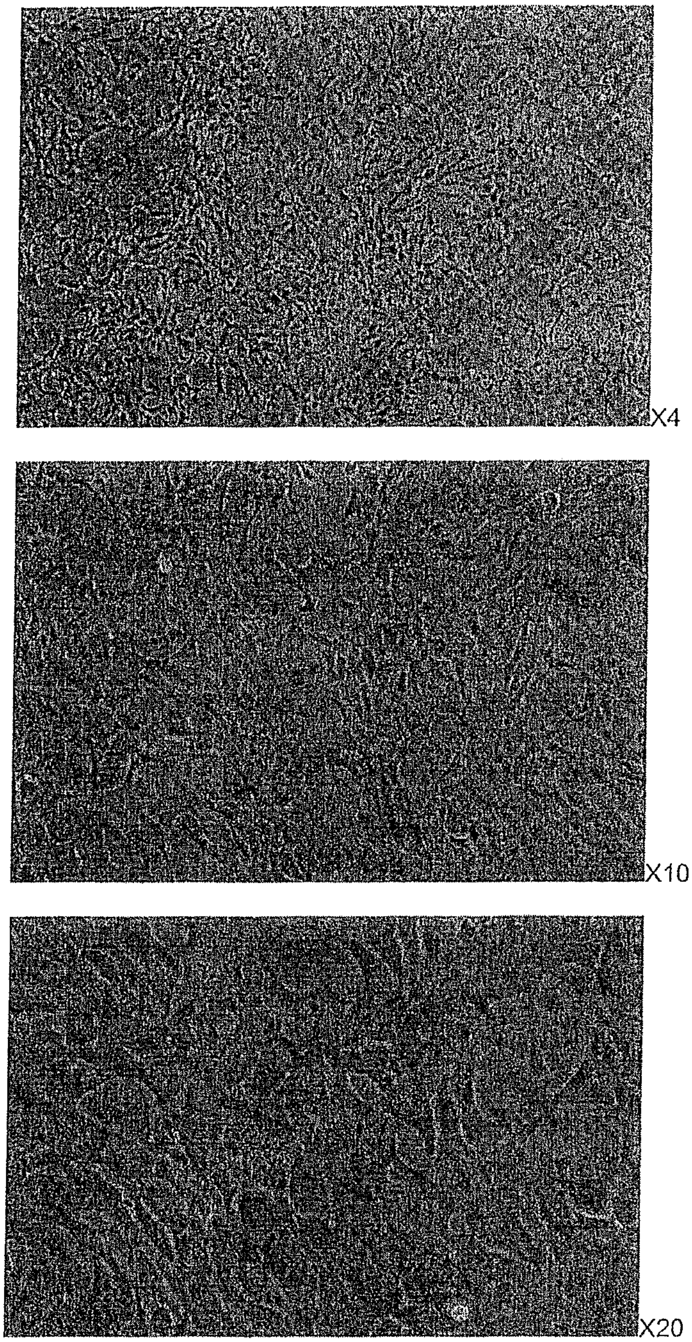
FIG. 5: depicts light microscopy imaging of T6-17490 (ECACC 08060501) (passage 45).
Figure 6:
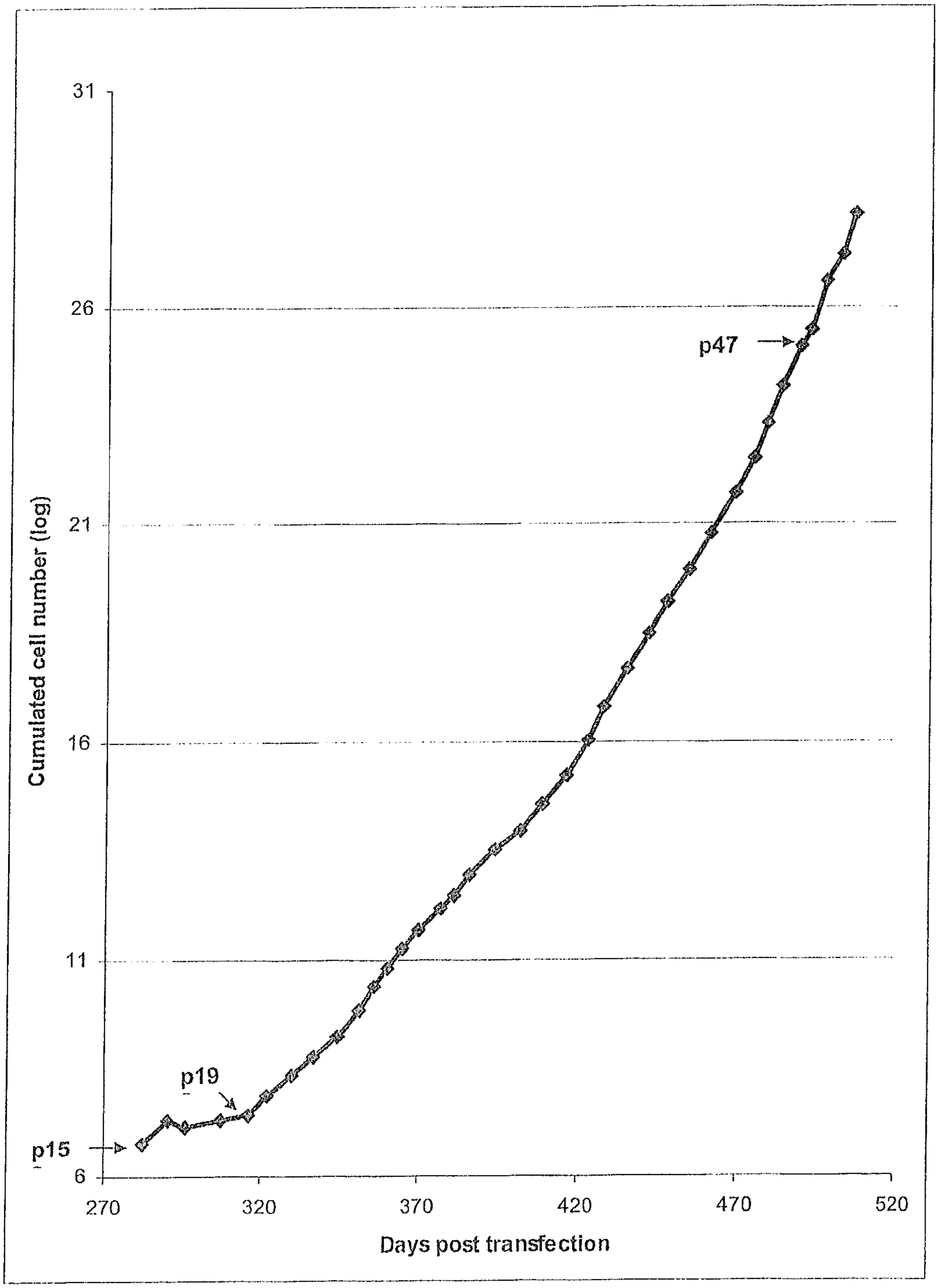
FIG. 6: T6-17490 (ECACC 08060501) *Cairina moschata* immortalized avian cell line growth curve (from passage 15 to passage 51).
Figure 7:
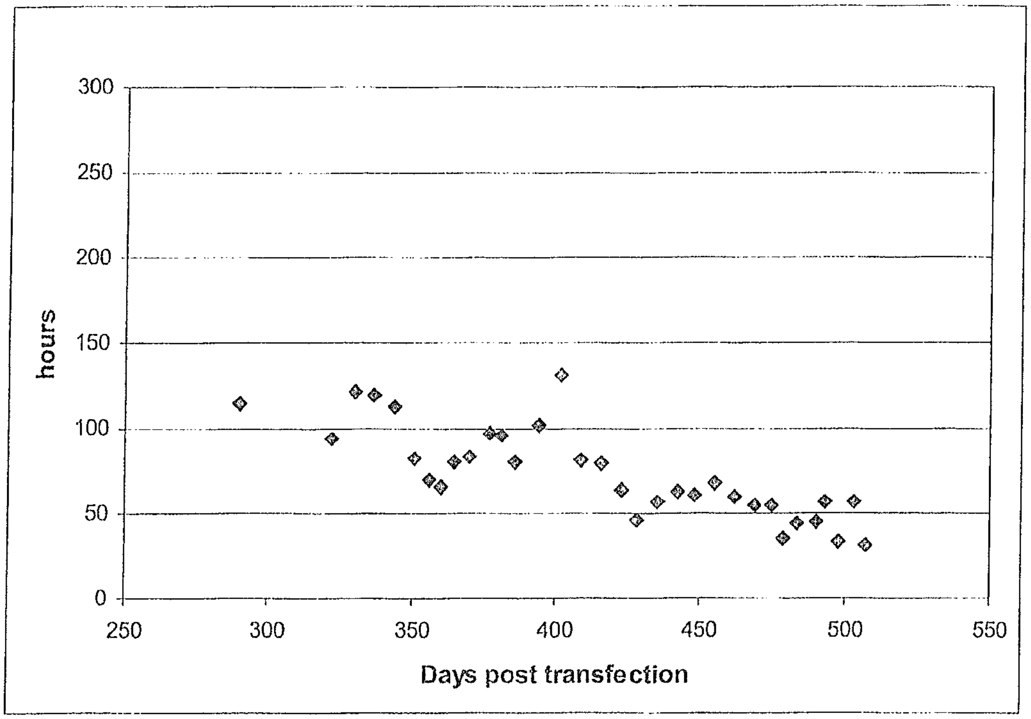
FIG. 7: T6-17490 (ECACC 08060501) *Cairina moschata* immortalized avian cell line population doubling time evolution (from passage 16 to passage 51).

T6-17490 Immortalized *Cairina Moschata* Cell Line (as Deposited at ECACC Under Accession Number 08060501) Used for the Production of an Orthopoxvirus According to the Method of the Invention T6-17490 cells (passage 45) have a homogenous fibroblast like morphology (FIG. 5). The static monolayer is stable up to 100% confluence and subject to contact inhibition. The cells were tested negative for mycoplasma contamination and for microbial contamination as well. The T6-17490 cell line growth curve (from passage 15 to passage 51) (FIG. 6) shows a continuous exponential growth phase from passage 19. During this period the measured population doubling time (PDT) was progressively decreasing. Average PDT passed from 94 h (passage 20 to 35) to 52 h (passage 36 to 51) (FIG. 7). The number of calculated population doublings (PDL) corresponding to the 51 passages is at least 71 population doublings. The T6-17490 cells are therefore far beyond the Hayflick limit and are consequently referred as immortalized cell line.

N.B.:

The population doubling level (PDL) refers to the number of cell generations (biomass 2 fold increase). PDL calculation: PDL=Ln(final/initial cell number)/Ln(2);

The population doubling time (PDT), also called generation time, is the time needed for one population doubling. PDT calculation: PDT=Δt*Ln(2)/Ln(final/initial cell number).

Example 4

Methode B

Step a'): Preparing a Culture of Packaging Cells.

Sixty six SPF eggs are incubated in for 60 secondes in a 2% formol solution. After being rinsed with 70% ethanol, the eggs are opened, the embryos are extracted and dissected. The obtained tissues are then digested at 36.5° C. for 120 minutes by dispase (UI/ml) and triple select (UI/ml). The mixture is filtrated to remove undigested tissues and the CEFs are collected by centrifugation (2300 rpm, 15 minutes). The CEFs are incubated in 55 L of VP-SFM (Invitrogen) for 2 days at 36.5° C.

Step b'): Infecting the Packaging Cell Culture with an Orthopoxvirus.

The cell culture media is then discarded and the MVA-[MUC1-IL2] also called TG4010 (0.05 MOI) (MVA deposited before Collection Nationale de Cultures de Microorganismes (CNCM) under depositary N° I-721) is added in 55 L of Basal Medium Eagle (Invitrogen).

Step c'): Culturing the Infected Packaging Cells Until Progeny Orthopoxvirus is Produced.

The infected CEFs are then incubated for three days at 36.5° C.

Step d'): Incubation in Presence of One or More Nucleases.

Infected CEFs comprising the MVA progeny are then incubated in presence of Benzonase® 10 U/ml (Merck; Reference 1.01653.0001) under the following conditions:

2 hours under agitation at a temperature of 25° C.;

$Mg^{2+}$ 2 mM;

pH of 8.0.

Step e'): Recovering the Orthopoxviruses from the Culture Supernatant and/or the Packaging Cells.

The cell culture media and the CEFs are collected. The mixture is then homogenised for 15 minutes at 11 ml/min with a Silverson© L4R high speed homogeniser (Silverson), or for 75 minutes at 1500 ml/min with a SONITUBE 36 kHz type SM 35/3WU (Heraeus PSP).

Step f'): Incubating the Orthopoxviruses Recovered in Step e') in Presence of One or More Agents Capable to Inhibit the Nuclease(s) Activity.

The obtained mixture is then incubated in presence of NaCl 100 mM and EDTA 10 mM, pH 8.0.

Step g'): Contacting the Mixture Obtained in Step f') with an Anion Exchange Adsorbent Under Suitable Conditions to Allow the Capture of said Orthopoxviruses and Nucleic Acids.

The obtained mixture is then added to BioSepra® Q hyperZ (Pall Corporation). The BioSepra® hyperZ (Pall Corporation) beads-formed matrix is first washed with sterile water, then sanitized with NaOH 0.5 N, washed with Tris 10 mM buffer (pH 8.0), and then equilibrated with Tris 10 mM NaCl 10 mM saccharose 5% buffer (pH 8.0).

The BioSepra® Q hyperZ (Pall Corporation) beads-formed matrix is then added by using a peristaltic Watson-Marlow pump (Reference 323ES/4D, 520S; Watson-Marlow) to the mixture obtained in step f') contained in a Flexboy® bag (Reference FFB101961; Sartorius Stedim biotech).

The BioSepra® Q hyperZ (Pall Corporation) beads-formed matrix and the mixture obtained in step f') are kept in contact during 1 hour under slow agitation at room temperature (20° C. to 22° C.).

Step h'): Clarifying the Mixture Obtained in Step g') Under Suitable Conditions to Allow the Withdrawal of the Cellular Debris.

The obtained mixture is then clarified by depth filtration on a Sartopure® PP2 8 μm (Sartorius) coupled to a Sartopure® PP2 5 μm (Sartorius) at a flow rate of 1 L/minute.

Step i'): Eluting the Orthopoxviruses with a Solution Comprising Monovalent Salts.

The Orthopoxviruses are eluted by an increasing NaCl concentration gradient (300 mM; 400 mM; 500 mM) in SO8 buffer (10 mM Tris-HCl; sucrose 5% (w/v); 10 mM sodium glutamate; 50 mM NaCl; pH 8.0 with physiological osmolarity (290 mOsm/kg)) by using a peristaltic Watson-Marlow pump (Reference 323ES/4D, 520S; Watson-Marlow).

Step j'): Concentrating the Mixture Obtained in Step i').

The eluat obtained in step i') is then concentrated 18 times through a 0.1 μm Prostak Microfiltration Module (Reference PSVVAG021, Millipore).

Step k'): Diafiltrating the Fraction Comprising the Orthopoxviruses Obtained in Step j').

The retentate is then diafiltred on the same module i.e. 0.1 μm Prostak Microfiltration Module (Reference PSVVAG021, Millipore).

The quantification of DNA is performed using Quant-iT™ Picogreen® dsDNA Assays Kit (Cat. No. P7589, Invitrogen).

Results: No remaining DNA is detected.

All documents (e.g. patents, patent applications, publications) cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A method for producing and purifying an Orthopoxvirus, comprising:

a) preparing a culture of packaging cells;

b) infecting the packaging cell culture with an Orthopoxvirus;

c) culturing the infected packaging cells until progeny Orthopoxvirus is produced;

d) incubating the cultured infected packaging cells in the presence of one or more nucleases;

e) recovering Orthopoxviruses from the culture supernatant and/or the packaging cells;

f) adding monovalent salts to the Orthopoxviruses recovered in step e) under conditions suitable to inhibit the nuclease(s) activity and to avoid the adsorption of said Orthopoxviruses to an anion exchange adsorbent; and, g) contacting the mixture obtained in step f) with said anion exchange adsorbent under conditions suitable to allow the capture of nucleic acids.

2. The method according to claim 1, wherein the packaging cells are immortalized cell lines.

3. The method according to claim 2, wherein the packaging cells are immortalized avian cell lines.

4. The method according to claim 2, wherein said immortalized cell lines are capable of growing in suspension without microcarriers.

5. The method according to claim 4, wherein said immortalized cell lines are capable of growing in suspension without microcarriers and wherein said cells are cultured in media free from animal products.

6. The method according to claim 1, wherein the packaging cells are primary or secondary avian cells.

7. The method according to claim 1, wherein the packaging cells are chicken embryo fibroblasts (CEFs).

8. The method according to claim 1, wherein the pH for carrying out step d) is between 7.0 and 9.0.

9. The method according to claim 8, wherein the pH is between 7.5 and 8.5.

10. The method according to claim 9, wherein the pH is 8.0.

11. The method according to claim 1, wherein the nuclease(s) is/are endonuclease(s).

12. The method according to claim 1, wherein the concentration of nuclease(s) is in the range of 5 to 100 U/ml.

13. The method according to claim 12, wherein the concentration of nuclease(s) is in the range of 5 to 50 U/ml.

14. The method according to claim 13, wherein the concentration of nuclease(s) is 10 U/ml.

15. The method according to claim 1, wherein the step of recovering the Orthopoxviruses is preceded by:

1) a step allowing the disruption of the packaging cell membrane; and 2) a step of incubation of the mixture obtained in step 1) for least 1 hour with the one or more nuclease(s) of step (d).

16. The method according to claim 1, wherein the anion exchange adsorbent is a beads-formed matrix having a diameter higher than 8 μm.

17. The method according to claim 16, wherein the anion exchange adsorbent consists in a beads-formed matrix having a diameter between 50 μm and 150 μm.

18. The method according to claim 17, wherein the anion exchange adsorbent is a beads-formed matrix having a diameter between 90 μm and 120 μm.

19. The method according to claim 18, wherein the anion exchange adsorbent is a beads-formed matrix having a diameter of 120 μm.

20. The method according to claim 1, wherein the functional groups of the anion exchange adsorbent are selected from the group consisting of dimethylaminoethyl (DMAE), diethylaminoethyl (DEAE), trimethylaminoethyl (TMAE), and triethylaminoethyl (TEAE).

21. The method according to claim 20, wherein the functional groups of the anion exchange adsorbent are trimethylaminoethyl (TMAE).

22. The method according to claim 1, wherein the monovalent salts used in step f) are NaCl.

23. The method according to claim 22, wherein the concentration of monovalent salts used in step f) is 50 to 150 mM.

24. The method according to claim 23, wherein the concentration of monovalent salts used in step f) is 100 mM.

25. The method according to claim 1, further comprising one or more additional purification steps.

26. The method according to claim 25, further comprising:

h) optionally clarifying the mixture obtained in step g) under suitable conditions to allow the withdrawal of the cellular debris;

i) washing the anion exchange adsorbent with a solution comprising monovalent salts under suitable conditions to recover Orthopoxviruses in the flow through; and, j) concentrating the flow through obtained in step g) or step h) and the flow through obtained in step i).

27. The method according to claim 26, wherein the clarification step is performed by depth filtration.

28. The method according to claim 26, wherein the clarification step is performed by depth filtration with filters having a pore size of 8 μm coupled to filters having a pore size of 5 μm.

29. The method according to claim 26, wherein the concentration step is performed by microfiltration with filters having a pore size between 0.09 and 0.15 μm.

30. The method according to claim 29, wherein the concentration step is performed by microfiltration with filters having a pore size of 0.1 μm.

31. The method according to claim 26, further comprising a diafiltration step performed with filters having a pore size between 0.09 and 0.15 μm.

32. The method according to claim 26, further comprising a diafiltration step performed over filters having a pore size of 0.1 μm.

33. The method according to claim 26, wherein the method further comprises:

1) a step of gel filtration; and 2) a step of diafiltration.

34. The method according to claim 1, wherein said Orthopoxvirus is a Vaccinia Virus or a modified Vaccinia Virus Ankara (MVA).

35. The method according to claim 25, wherein said Orthopoxvirus is a Vaccinia Virus or a modified Vaccinia Virus Ankara (MVA).

36. The method according to claim 26, wherein said Orthopoxvirus is a Vaccinia Virus or a modified Vaccinia Virus Ankara (MVA).

37. The method according to claim 33, wherein said Orthopoxvirus is a Vaccinia Virus or a modified Vaccinia Virus Ankara (MVA).

38. A method for producing and purifying an Orthopoxvirus, comprising recovering Orthopoxviruses from cultured packaging cells infected with the Orthopoxvirus and/or a culture supernatant of such cultured packaging cells; the improvement comprising:

i) incubating the cultured infected packaging cells in the presence of one or more nucleases before recovering said Orthopoxviruses;

ii) adding monovalent salts to the recovered Orthopoxviruses under conditions suitable to inhibit said nuclease(s) and to avoid the adsorption of said Orthopoxviruses to an anion exchange adsorbent; and, iii) contacting the mixture obtained in step ii) with said anion exchange adsorbent under conditions suitable to allow the capture of nucleic acids.

39. The method according to claim 38, wherein the packaging cells are immortalized cell lines.

40. The method according to claim 38, wherein the packaging cells are immortalized avian cell lines.

41. The method according to claim 39, wherein said immortalized cell lines are capable of growing in suspension without microcarriers.

42. The method according to claim 41, wherein said immortalized cell lines are capable of growing in suspension without microcarriers and wherein said cells are cultured in media free from animal products.

43. The method according to claim 38, wherein the packaging cells are primary or secondary avian cells.

44. The method according to claim 38, wherein the packaging cells are chicken embryo fibroblasts (CEFs).

45. The method according to claim 38, wherein the pH for carrying out step d) is between 7.0 and 9.0.

46. The method according to claim 45, wherein the pH is between 7.5 and 8.5.

47. The method according to claim 46, wherein the pH is 8.0.

48. The method according to claim 38, wherein the nuclease(s) is/are endonuclease(s).

49. The method according to claim 38, wherein the concentration of nuclease(s) is in the range of 5 to 100 U/ml.

50. The method according to claim 49, wherein the concentration of nuclease(s) is in the range of 5 to 50 U/ml.

51. The method according to claim 50, wherein the concentration of nuclease(s) is 10 U/ml.

52. The method according to claim 38, wherein the anion exchange adsorbent is a beads-formed matrix having a diameter higher than 8 μm.

53. The method according to claim 52, wherein the anion exchange adsorbent consists in a beads-formed matrix having a diameter between 50 μm and 150 μm.

54. The method according to claim 53, wherein the anion exchange adsorbent is a beads-formed matrix having a diameter between 90 μm and 120 μm.

55. The method according to claim 54, wherein the anion exchange adsorbent is a beads-formed matrix having a diameter of 120 μm.

56. The method according to claim 38, wherein the functional groups of the anion exchange adsorbent are selected from the group consisting of dimethylaminoethyl (DMAE), diethylaminoethyl (DEAE), trimethylaminoethyl (TMAE), and triethylaminoethyl (TEAE).

57. The method according to claim 56, wherein the functional groups of the anion exchange adsorbent are trimethylaminoethyl (TMAE).

58. The method according to claim 38, wherein the monovalent salts used in step f) are NaCl.

59. The method according to claim 58, wherein the concentration of monovalent salts used in step f) is 50 to 150 mM.

60. The method according to claim 59, wherein the concentration of monovalent salts used in step f) is 100 mM.

61. The method according to claim 38, further comprising one or more additional purification steps.

62. The method according to claim 61, further comprising:

iv) optionally clarifying the mixture obtained in step iii) under suitable conditions to allow the withdrawal of the cellular debris;

v) washing the anion exchange adsorbent with a solution comprising monovalent salts under suitable conditions to recover Orthopoxviruses in the flow through; and, vi) concentrating the flow through obtained in step iii) or step iv) and the flow through obtained in step v).

63. The method according to claim 62, wherein the clarification step is performed by depth filtration.

64. The method according to claim 63, wherein the clarification step is performed by depth filtration with filters having a pore size of 8 μm coupled to filters having a pore size of 5 μm.

65. The method according to claim 62, wherein the concentration step is performed by microfiltration with filters having a pore size between 0.09 and 0.15 μm.

66. The method according to claim 65, wherein the concentration step is performed by microfiltration with filters having a pore size of 0.1 μm.

67. The method according to claim 62, further comprising a diafiltration step performed with filters having a pore size between 0.09 and 0.15 μm.

68. The method according to claim 67, further comprising a diafiltration step performed over filters having a pore size of 0.1 μm.

69. The method according to claim 38, wherein said Orthopoxvirus is a Vaccinia Virus or a modified Vaccinia Virus Ankara (MVA).

70. The method according to claim 61, wherein said Orthopoxvirus is a Vaccinia Virus or a modified Vaccinia Virus Ankara (MVA).

71. The method according to claim 62, wherein said Orthopoxvirus is a Vaccinia Virus or a modified Vaccinia Virus Ankara (MVA).

* * * * *